(12) United States Patent
Ferwerda et al.

(10) Patent No.: US 12,296,194 B2
(45) Date of Patent: May 13, 2025

(54) SENSING APPARATUS

(71) Applicant: NUCLETRON OPERATIONS B.V., Veenendaal (NL)

(72) Inventors: Sjoerd Ferwerda, Veenendaal (NL); Martin van Beek, Veenendaal (NL)

(73) Assignee: Nucletron Operations B.V., Veenendaal (NL)

( * ) Notice: Subject to any disclaimer, the term of this patent is extended or adjusted under 35 U.S.C. 154(b) by 439 days.

(21) Appl. No.: 17/632,080

(22) PCT Filed: Aug. 3, 2020

(86) PCT No.: PCT/NL2020/050493
§ 371 (c)(1),
(2) Date: Feb. 1, 2022

(87) PCT Pub. No.: WO2021/025553
PCT Pub. Date: Feb. 11, 2021

(65) Prior Publication Data
US 2022/0273966 A1    Sep. 1, 2022

(30) Foreign Application Priority Data

Aug. 2, 2019 (NL) ...................................... 2023605

(51) Int. Cl.
*A61N 5/10* (2006.01)
(52) U.S. Cl.
CPC ......... *A61N 5/1048* (2013.01); *A61N 5/1007* (2013.01); *A61N 2005/1008* (2013.01)
(58) Field of Classification Search
None
See application file for complete search history.

(56) References Cited

U.S. PATENT DOCUMENTS

| 4,851,694 A | 7/1989 | Rague et al. |
| 2006/0133575 A1* | 6/2006 | Gutman ............... A61N 5/1001 378/65 |

(Continued)

FOREIGN PATENT DOCUMENTS

| CN | 204855900 U | 12/2015 |
| WO | 2008025566 | 3/2008 |

OTHER PUBLICATIONS

"International Application Serial No. PCT/NL2020/050493, International Search Report dated Oct. 29, 2020", (Oct. 29, 2020), 4 pgs.

(Continued)

*Primary Examiner* — Hoon K Song
(74) *Attorney, Agent, or Firm* — Schwegman Lundberg & Woessner, P.A.

(57) ABSTRACT

A sensing apparatus for sensing the presence of a radioactive source, or check-dummy- or sensor cable, at a point along the sensing apparatus during a brachytherapy procedure. The sensing apparatus comprises a transfer tube comprising a first end and a second end. The second end being downstream of the first end. The sensing apparatus further comprises sensing means operable to detect the presence of a radioactive source, or check-dummy- or sensor cable, at a point downstream of the first end of the transfer tube. The reason for the plurality of "prisms" or the semispheres, is that they are orientation independent to the light fibers, simplifying assembly. Alternatively the plurality of prisms may be substituted by two half-spherical "prisms". Between the prisms, a light blocking surface need to be placed to avoid optical short circuits.

14 Claims, 14 Drawing Sheets

(56) References Cited

U.S. PATENT DOCUMENTS

| | | |
|---|---|---|
| 2006/0135843 A1 | 6/2006 | Heath |
| 2007/0129593 A1 | 6/2007 | Gueye et al. |
| 2014/0005465 A1 | 1/2014 | Ribbing |
| 2016/0339267 A1* | 11/2016 | Woudstra ............. A61N 5/1007 |
| 2017/0007849 A1* | 1/2017 | Hautvast ............. A61N 5/1001 |
| 2022/0209464 A1* | 6/2022 | Schneider ............ H01R 13/641 |

OTHER PUBLICATIONS

"European Application No. 20750782.3, Examination Report dated Nov. 20, 2024", (Nov. 20, 2024), 3 pgs.

* cited by examiner

SENSING APPARATUS

PRIORITY APPLICATIONS

This application is a U.S. National Stage Filing under 35 U.S.C. § 371 from International Application No. PCT/NL2020/050493, filed on Aug. 3, 2020, and published as WO2021/025553 on Feb. 11, 2021, which claims the benefit of priority to Netherlands Application No. 2023605, filed on Aug. 2, 2019; the benefit of priority of each of which is hereby claimed herein, and which applications and publication are hereby incorporated herein by reference in their entireties.

FIELD

This disclosure relates to brachytherapy, in particular to a sensing apparatus for sensing the presence of an article, such as a radioactive source, at a point along a transfer tube during a brachytherapy procedure.

BACKGROUND

Brachytherapy is a type of radiotherapy in which a source of radiation is placed inside a patient's body and arranged proximate to the region of the body requiring treatment. A key advantage of brachytherapy over other types of radiotherapy, such as external beam radiotherapy (EBRT), is that the radiation source spends most of its time inside the body in close proximity with the cells requiring treatment. As a result, healthy cells not requiring treatment are exposed to less radiation than in other radiotherapy procedures, such as EBRT. This reduces the damage caused to such healthy cells and, consequently, reduces the adverse side effects experienced by the patient.

Accurate positioning of the radiation source next to the region of the body requiring treatment is therefore a crucial aspect of the brachytherapy procedure, and is particularly important for high dose rate brachytherapy procedures. The accurate positioning of the radiation source is an essential part of the quality assurance (QA) for any brachytherapy treatment.

One of the known approaches for positioning the radiation source in the body is to use a stepper motor. In more detail, in such known approaches, a stepper motor is used to advance the radioactive source from a radiation safe of an afterloader to an applicator positioned inside the patient's body via a transfer tube. Such stepper motors are controllable to provide a discrete number of precise fractions of rotations, and each discrete movement or step of the stepper motor causes the radioactive source to move by a known amount. As a result, the advancing of the radioactive source from the radiation safe to the applicator can be controlled by controlling the number of steps of the stepper motor. The number of steps is typically based on a predetermined linear distance between the radiation safe and the desired position of the radioactive source in the applicator.

A problem with this known approach, however, is that the arrangement of the transfer tube often varies between radiotherapy sessions. For example, the degree of curvature of the transfer tube can vary from one radiotherapy session to the next due to variances in apparatus setup. In addition, the dimensions of the transfer tube can vary due to variances in ambient air temperature. As a result, the length of the actual travel path of the radioactive source through the transfer tube will vary. For example, when the transfer tube is curved, the travel path will be of a different length than if the transfer tube is straight due to the tendency of the cable attached to the radioactive source, to follow the outer corners of the curved transfer tube. Consequently, the length of the actual overall travel path of the radioactive source from the radiation safe to the desired position in the applicator will vary between sessions and from the predetermined linear distance. Accordingly, a problem with this known approach is that it is difficult to accurately position the radioactive source at the desired point in the applicator.

One known way of addressing this problem is to arrange the transfer tube so that it is as straight and taut as possible. This can be achieved in various ways: for example, by laying the transfer tube flat on a surface, or by incorporating springs into the transfer tube assembly to provide rigidity. However, in practice, variations in the arrangement of the transfer tube will still exist and so there will still be some variation in the length of the actual travel path of the radioactive source through the transfer tube. As a result, it is still difficult to accurately position the radioactive source at the desired point in the applicator. US2017007849 addresses a system and method wherein an applicator is provided defining an applicator lumen comprising sensor elements, that generate an output signal indicative whether or not the radiation source is at a predetermined position in the lumen. US'849, while disclosing a method to signal whether or not a radiation source is at a predetermined position in the lumen is dependent on specifically crafted applicators that depend on the radiation source being present in prescribed locations that can be detected by sensors.

It remains a challenge to have an article accurately positioned inside the applicator regardless of the practical set up of the transfer tube and applicator.

The present invention seeks to address these and other disadvantages encountered in the prior art by providing an improved approach towards sensing the position of a radioactive source.

SUMMARY

In a first aspect, there is provided a transfer tube through which an article may travel for use in a brachytherapy procedure, the transfer tube comprising:
  a first end connectable to an afterloader; and
  a second end connectable to an applicator, the second end being downstream of the first end; and
  signal transfer means operable with sensing means to detect the presence of the article at a point downstream of the first end of the transfer tube, wherein the signal transfer means is operable with the sensing means to detect the presence of the article as it exits the transfer tube via the second end.

The article may comprise a radioactive source, a check cable, a dummy cable, or a sensor cable. The check cable, the dummy cable and the sensor cable may each comprise a check cable tip, a dummy cable tip and a sensor cable tip, respectively.

In a further aspect a sensing apparatus may further comprise a light source and the transfer tube may further comprise: a first optical fibre configured to receive light from the light source and transfer the light to light transfer means located at the point, the light transfer means being configured to transfer the light from the first optical fibre to a second optical fibre; and wherein the second optical fibre is configured to transfer the light from the light transfer means to the sensing means.

The first end of the transfer tube may be connectable or be configured to connect to the afterloader via a transfer tube coupling. The afterloader transfer tube coupling may be connectable or be configured to connect to the afterloader via an adaptor alternatively.

The first end of the transfer tube may be connectable or be configured to connect to the afterloader via an adaptor.

The second end of the transfer tube may be connectable or be configured to connect to an applicator transfer tube coupling. The transfer tube may comprise signal transfer means operable with the sensing means to detect the presence of the article at the or a point along the transfer tube. The signal transfer means may be arranged substantially at the second end of the transfer tube. In use, the signal transfer means may be arranged within the applicator transfer tube coupling.

In a second aspect, there is provided a transfer tube through which the article may travel for use in a brachytherapy procedure, the transfer tube comprising: a first end connectable to an afterloader; and a second end connectable to an applicator, the second end being downstream of the first end; and signal transfer means operable with sensing means to detect the presence of the article at a point downstream of the first end of the transfer tube.

The signal transfer means may be operable with the sensing means to detect the presence of the article as it exits the transfer tube via the second end.

The transfer tube may define at least part of a path along which the article may travel. The signal transfer means may be configured to transfer a signal across the path which may be interrupted by the presence of the article at the point. The signal transfer means may comprise at least two optical fibres. The at least two optical fibres may be embedded in the wall of the transfer tube. The two optical fibres may be embedded in opposite sides of the wall of the transfer tube.

The signal transfer means may further comprise light transfer means arranged at the point. The at least two optical fibres may be coupled with the light transfer means. At least one of the at least two optical fibres may be coupled with the sensing means.

A first optical fibre of the at least two optical fibres may be configured to receive light from a light source and transfer the light to the light transfer means. The light transfer means may be configured to transfer the light from the first to a second optical fibre of the at least two optical fibres. The second optical fibre may be configured to transfer the light from the light transfer means to the sensing means.

In use, the article may travel from the afterloader, into the transfer tube at the first end of the transfer tube, along the transfer tube to the second end of the transfer tube, and into the applicator, such that the second end of the transfer tube and the applicator are downstream of the first end of the transfer tube. Optionally, there may be one or more further components between the afterloader, transfer tube and/or applicator. For example, there may be one or more coupling components between the afterloader, transfer tube and/or applicator. The article may additionally travel through these one or more further components.

The point may be located nearer to the second end of the transfer tube than the first end of the transfer tube. The point may be located at the second end of the transfer tube.

The transfer tube may be formed of flexible material.

The sensing means may be a sensor. The sensor may be a proximity sensor, an infrared sensor, a pressure sensor, an optical sensor, an ultrasonic sensor and/or a camera. The camera may be an optical camera.

The light transfer means may further comprise a plurality of light directing elements arranged about the diameter of the transfer tube.

Each of the plurality of light directing elements may be configured to: collect light from one of the optical fibres and transfer the light to at least one other of the plurality of light directing elements; and collect light from the at least one other of the plurality of light directing elements and transfer the light to the one optical fibre.

Each of the light directing elements comprises a surface arranged to: receive light from one of the optical fibres, wherein light is received at the surface from the one optical fibre at an angle of incidence of substantially 45 degrees; and reflect light received from the one of the optical fibres towards another of the plurality of light directing elements.

Each of the surfaces may be further arranged to: receive light from another of the plurality of light directing elements, wherein light is received at the surface at an angle of incidence of substantially 45 degrees; and reflect light received from the other of the plurality of light directing elements towards one of the optical fibres.

The light transfer means may be arranged such that the article may travel through the light transfer means.

The sensing apparatus may comprise further light transfer means arranged to: transfer light from a light source to one of the optical fibres; and transfer light from the other of the optical fibres to the sensing means.

The light source may be a light-emitting device, such as light-emitting diode.

The afterloader may comprise the light source and/or the sensing means.

The further light transfer means may comprise a first further light directing element and a second further light directing element.

The first further light directing element may be arranged to collect light from one of the optical fibres and transfer light collected from the one optical fibre to the sensing means.

The first further light directing element may comprise a surface arranged to: receive light from the one of the optical fibres, wherein light is received at the surface at an angle of incidence of substantially 45 degrees; and reflect light received from the one of the optical fibres towards the sensing means.

The second further light directing element may be arranged to collect light from the light source and transfer light collected from the light source to the other of the optical fibres.

The second further light directing element may comprise a surface arranged to: receive light from the light source, wherein light is received at the surface at an angle of incidence of substantially 45 degrees; and reflect light received from the light source towards the other of the optical fibres.

In use, the sensing means may detect the presence of the article at the point along the transfer tube when no light is received at the sensing means.

The transfer tube may comprise at least one supporting member. The supporting member may be embedded in the wall of the transfer tube. The supporting member may extend at least partially along the length of the transfer tube. The supporting member may extend along the full length of the transfer tube. The support member may extend from the first end to the second end of the transfer tube. The transfer tube may comprise a plurality of supporting members. The plurality of supporting members may be equally spaced around the diameter of the wall of the transfer tube. The transfer tube may comprise two supporting members and the two supporting members may be arranged in opposing sides of the wall of the transfer tube. The supporting members may be supporting wires.

The supporting members may be arranged to provide rigidity to the transfer tube.

The sensing apparatus may further comprise a drive mechanism operable to drive the article through the transfer tube.

The sensing apparatus may further comprise control means operable to control the drive mechanism.

The drive mechanism may be operable, under control of the control means, to drive the article to the point along the transfer tube and to drive the article to a predetermined distance from the point along the transfer tube.

The drive mechanism may be a stepper motor. The control means may be a closed loop control system.

The sensing means may be configured to send to the control means a signal indicating that the article is at the point along the transfer tube.

Upon receipt of the signal indicating that the article is at the point along the transfer tube, the control means may be configured to send an instruction to the drive mechanism to drive the article the predetermined distance from the point.

Upon receipt of the instruction to drive the article the predetermined distance from the point, the drive mechanism may be configured to drive the article the predetermined distance from the point.

When the drive mechanism is a stepper motor, the predetermined distance may be a number of steps of the stepper motor.

The point along the transfer tube may be a zero-reference point. In a further aspect a zero reference point controller may be arranged to control the progression of the article into the applicator relative to the zero reference point formed by the point downstream of the first end of the transfer tube, by an instruction to drive the article a predetermined distance from the point by the drive mechanism.

In a third aspect, there is provided a method of sensing the presence of an article at a point along a transfer tube during a brachytherapy procedure, the transfer tube comprising: a first end connectable to an afterloader; a second end, wherein the article may enter the transfer tube through the first end and exit the transfer tube through the second end; and detection means operable with sensing means to detect the presence of the article at a point along the transfer tube, the method comprising the steps of: sending, from a source, a signal to the detection means; determining if the signal is received at the sensing means; and if the signal is not received at the sensing means, determining that the article is at the point along the transfer tube and controlling, by a zero reference point controller, the progression of the article into the applicator relative to a zero reference point formed by the point downstream of the first end of the transfer tube, by sending, from the controller, an instruction to drive the article a predetermined distance from the point.

In a fourth aspect, there is provided a method of sensing the presence of an article at a point along brachytherapy apparatus during a brachytherapy procedure, the brachytherapy apparatus defining a path along which the article may travel and comprising: a transfer tube comprising a first end connectable to an afterloader and a second end connectable to an applicator, the second end being downstream of the first end; and signal transfer means operable with sensing means to detect the presence of the article at the point downstream of the first end of the transfer tube, the method comprising: sending, from a source, a signal to the sensing means via the signal transfer means; the signal transfer means being configured to transfer the signal across the path; determining if the signal is received at the sensing means; and if the signal is not received at the sensing means, determining that the article is at the point downstream of the first end of the transfer tube.

The step of sending, from the source, the signal to the sensing means via the signal transfer means may comprise continually sending the signal to the signal transfer means.

The method may further comprise the step of: if the signal is not received at the sensing means, sending, from the sensing means to control means, a signal indicating that the article is at the point downstream of the first end of the transfer tube. The control means may be operable to control a drive mechanism and the drive mechanism may be operable to drive the article through the brachytherapy apparatus.

The method may further comprise the step of: upon receipt at the control means of the signal indicating that the article is at the point downstream of the first end of the transfer tube, sending, from the control means to the drive mechanism, an instruction to drive the article a predetermined distance from the point.

The method may further comprise the step of: upon receipt at the drive mechanism of the instruction to drive the article the predetermined distance from the point, driving, by the drive mechanism, the article the predetermined distance from the point.

In a fifth aspect, there is provided a computer-readable medium comprising computer executable instructions for carrying out the method of the third aspect and/or the fourth aspect.

In a fifth aspect both the sensing apparatus and the drive mechanism are connected to a drive controller to manage the third and/or fourth aspects.

In a sixth aspect, there is provided a sensing apparatus for sensing the presence of an article at a point along a tube, the apparatus comprising: a tube through which the article may travel, the tube comprising a first end and a second end, the second end being downstream of the first end; and sensing means operable to detect the presence of the article at a point downstream of the first end.

The point may be located along the transfer tube. The point may be located between the first end and the second ends of the transfer tube.

The first end may be connectable or configured to connect to feeder apparatus. The article may enter the tube through the first end from the feeder apparatus (typically called Afterloader) and exit the transfer tube through the second end. The feeder apparatus may comprise the sensing means.

In a seventh aspect, there is provided a tube through which an article may travel, the tube comprising: a first end connectable to feeder apparatus; a second end, the second end being downstream of the first end; and signal transfer means operable with sensing means to detect the presence of the article at the point downstream of the first end of the tube.

The article may enter the tube through the first end from the feeder apparatus and exit the tube through the second end.

In an eighth aspect, there is provided a sensing apparatus for sensing the presence of an article at a point along a transfer tube or an applicator during a brachytherapy procedure, the apparatus comprising: a transfer tube through which the article may travel, the transfer tube comprising a first end and a second end, the first end being connectable to an afterloader, wherein the article may enter the transfer tube through the first end and exit the transfer tube through the second end; an applicator through which the article may travel, the applicator comprising a first end and a second end, the first end being connectable to the second end of the transfer tube; and sensing means operable to detect the presence of the article at a point at or between the first end of the transfer tube and the second end of the applicator.

The transfer tube and/or applicator may each comprise signal transfer means operable with the sensing means to detect the presence of the article at the point along the transfer tube and/or applicator.

In a ninth aspect, there is provided a transfer tube and an applicator through which the article may travel for use in a brachytherapy procedure. The transfer tube comprising: a first end connectable to an afterloader; a second end connectable to the applicator, wherein the article may enter the transfer tube through the first end and exit the transfer tube through the second end; and signal transfer means operable with sensing means to detect the presence of the article at a point along the transfer tube. The applicator comprising: a first end connectable to the transfer tube, wherein the article may enter the applicator through the first end; and signal transfer means operable with sensing means to detect the presence of the article at a point along the applicator.

In a tenth aspect, there is provided a sensing apparatus for sensing the presence of the article at a point along the sensing apparatus during a brachytherapy procedure, the apparatus comprising: an applicator through which the article may travel, the applicator comprising a first end and a second end; a transfer tube through which the article may travel, the transfer tube comprising a first end and a second end, the first end being connectable to an afterloader and the second end being connectable to the first end of the applicator; and sensing means operable to detect the presence of the article at a point between the first end of the transfer tube and the second end of the applicator.

In an eleventh aspect, there is provided a drive controller configured to carry out the method of the third aspect and/or the fourth aspect.

The drive controller may be arranged to communicatively couple with the sensing apparatus of the first aspect and the drive mechanism.

Optional features of aspects may equally well apply to other aspects.

BRIEF DESCRIPTION OF THE DRAWINGS

Specific implementations are now described, by way of example only, with reference to the drawings, in which.

Like numerals are used in the figures to describe like parts.

DETAILED DESCRIPTION OF THE DRAWINGS

The present disclosure relates, generally, to a sensing apparatus which can be used to detect the presence of an article, such as a cable (for example, a check cable) or a radioactive source, at a point along a transfer tube of a brachytherapy apparatus. In particular, the apparatus can be used to detect the presence of an article near or at the end of the transfer tube which is connected, in use, to an applicator (herein referred to as 'the second end').

As explained in detail below, the sensing apparatus is based on a 'light switch' principle. Once the presence of an article at a certain point in the transfer tube has been detected, this point can be regarded as the 'zero-reference point' and article can be advanced a predetermined distance from this zero-reference point.

A key advantage of this approach is that the article may be accurately positioned inside the applicator regardless of the practical set up of the transfer tube. This is because the article is advanced by the predetermined distance from the zero-reference point in the transfer tube, and not from the afterloader, for example. As a result, variations in the path of the article occurring before the zero-reference point are rendered unimportant as they do not affect the overall accuracy of the positioning of the article in the applicator (and thus, ultimately, human body).

Prior Art Brachytherapy System

A prior art brachytherapy system will now be described to provide context to the solution of the present disclosure.

Figure 1:
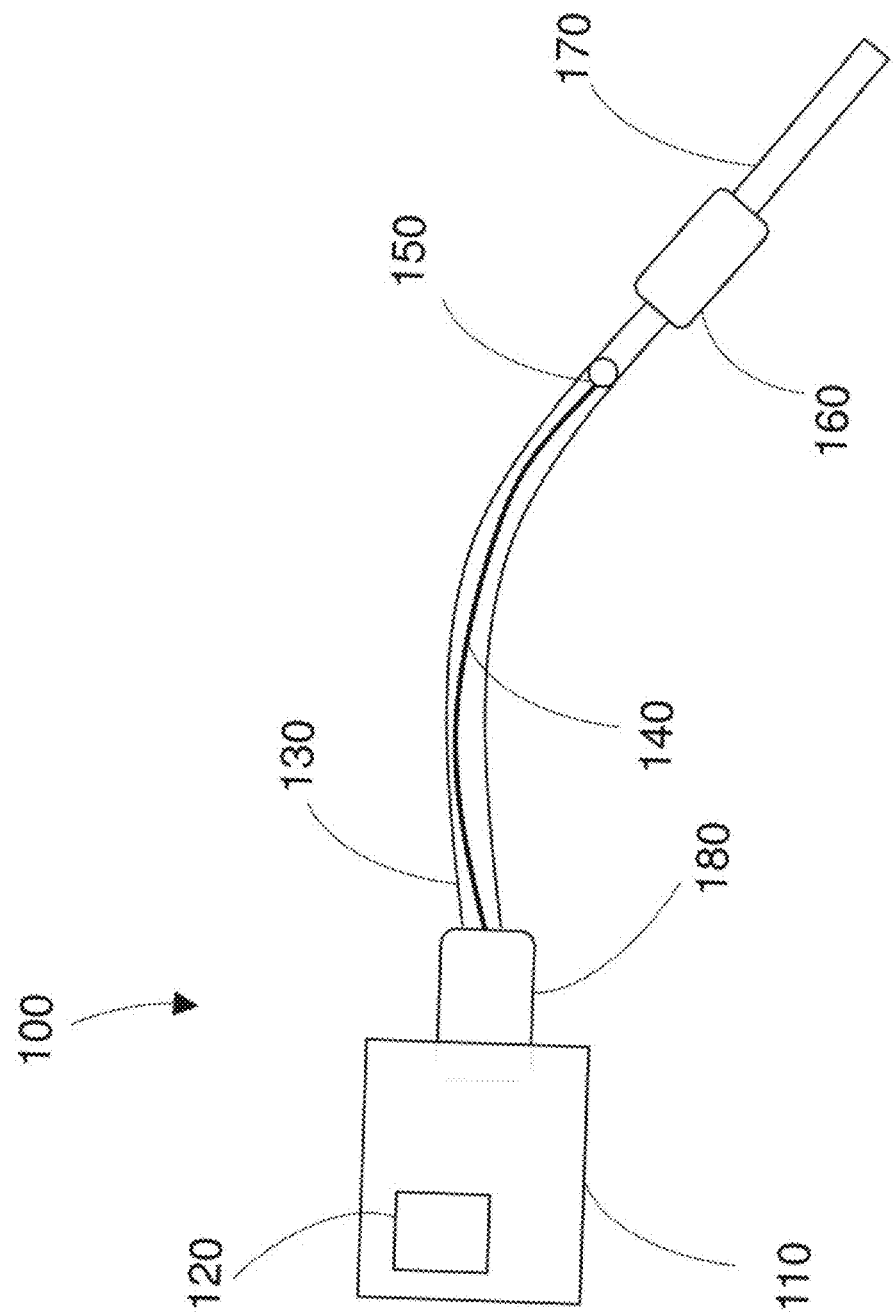
FIG. 1 is a schematic of a prior art brachytherapy system.

FIG. 1 shows a prior art brachytherapy system 100. The brachytherapy system includes an afterloader 110. When the brachytherapy system 100 is not in use, the afterloader 110 houses a radiation source 150 in a radiation safe. When the system 100 is in use, the afterloader 100 advances the radiation source 150 from the radiation safe to an applicator 170 for insertion into a human body. The radiation source 150 is attached to the end of a cable 140 which is driven from the afterloader 110. To this end, the afterloader 110 includes a drive system 120 for driving the cable 140 and radiation source 150 from the afterloader 110 to the applicator 170. The drive system 120 can be any kind of motor: for example, a stepper-motor.

The afterloader 110 is connected to the applicator 170 via a prior art transfer tube 130.

The prior art transfer tube 130 has a first end and a second end. The transfer tube 130 is connected at its first end to the afterloader 110 by an afterloader transfer tube coupling 180, and at its second end to the applicator 170 by an applicator transfer tube coupling 160.

The internal diameter of the prior art transfer tube 130 is such that the cable 140 and the radiation source 150 may pass comfortably through and along the length of the prior art transfer tube 130.

In use, the applicator 170 is inserted inside the patient's body such that the radiation source 150 may be positioned close to the region requiring treatment. The applicator 170 may be, for example, a needle, a canular, or any other device suitable for insertion into the patient's body. Once the applicator 170 is in position, the article 150 is advanced from the afterloader 110 to the applicator 170 along the prior art transfer tube 130. As discussed in the background section, for effective treatment of the region requiring treatment, accurate positioning of the radiation source 150 inside the applicator 170—and thus patient's body—is crucial. It is commonly accepted in the art that the transfer tube 130 must be arranged between the after loader 110 and applicator 170 in a manner as straight and taut as possible so as to ensure that the distance of advancement of the radiation source 150 as recorded by the drive system 120 matches the actual distance which the radiation source 150 travels from the afterloader 110 and along the transfer tube 130 and applicator 170. However, there may nevertheless be some 'snaking' of the cable 140 inside the transfer tube 130, or even small variations in the length of the transfer tube 130. It is this problem, in part, that the present disclosure seeks to address.

Solution—Single Point Sensing

A detailed description of a solution of the present disclosure will now be given.

Figure 2:
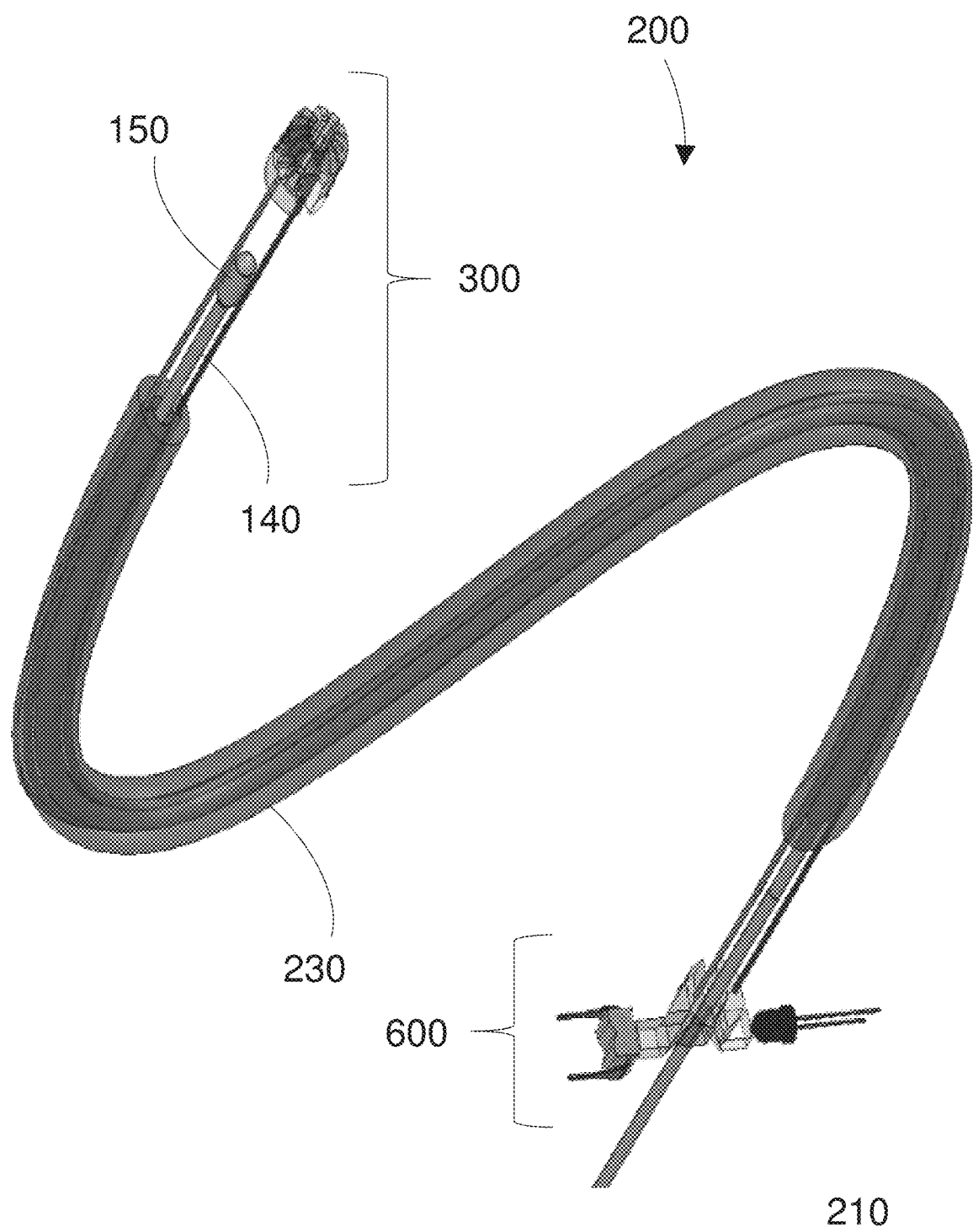
FIG. 2 is an axonometric view of components of a sensing apparatus that is a first implementation.

FIG. 2 shows an axonometric view of components of a sensing apparatus 200 in accordance with a first implementation of the disclosure. The sensing apparatus 200 includes a transfer tube 230. As for the prior art transfer tube 130 described in relation to FIG. 1, the inner diameter of the transfer tube 230 is suitably dimensioned to allow for the passage of the cable 140 and radiation source 150 along the length of the transfer tube 230. FIG. 2 shows a cable 140 and radiation source 150 passing through the transfer tube 230. Unlike the prior art transfer tube 130 however, the transfer tube 230 of the present disclosure includes additional features, which will be described in more detail in relation to FIG. 3.

Returning to what is shown in FIG. 2, the transfer tube 230 comprises a first end and a second end. The first end of the transfer tube 230 interfaces with sensor system 600. The sensor system 600 will be described in more detail in relation to FIG. 6. The first end of the transfer tube 230, which interfaces with the sensor system 600, is the end of the transfer tube 230 which, in use, is coupled or connected with the afterloader 110 via the afterloader transfer tube coupling 180.

The second end of the transfer tube 230 comprises signal transfer means 300. That is, in this implementation, the signal transfer means 300 is arranged at or near the second end of the transfer tube 230. The signal transfer means 300 may also be referred to as a signal transferer, signal transfer equipment or signal transfer apparatus. The signal transfer means 300 will be described in more detail in relation to FIGS. 3 and 4. The second end of the transfer tube 230, which comprises the signal transfer means 300, is the end of the transfer tube 230 which, in use, is coupled or connected with the applicator 170 via the transfer tube coupling 160.

The transfer tube 230 defines at least part of a path along which, in use, the article may travel. The path extends from the afterloader 110 to the applicator 170 via the transfer tube. The second end of the transfer tube 230 is considered in this disclosure as being downstream of the first end of the transfer tube 230. For consistency, the applicator 170 is thus also considered in this disclosure as being downstream of the first end of the transfer tube 230.

Figure 3:
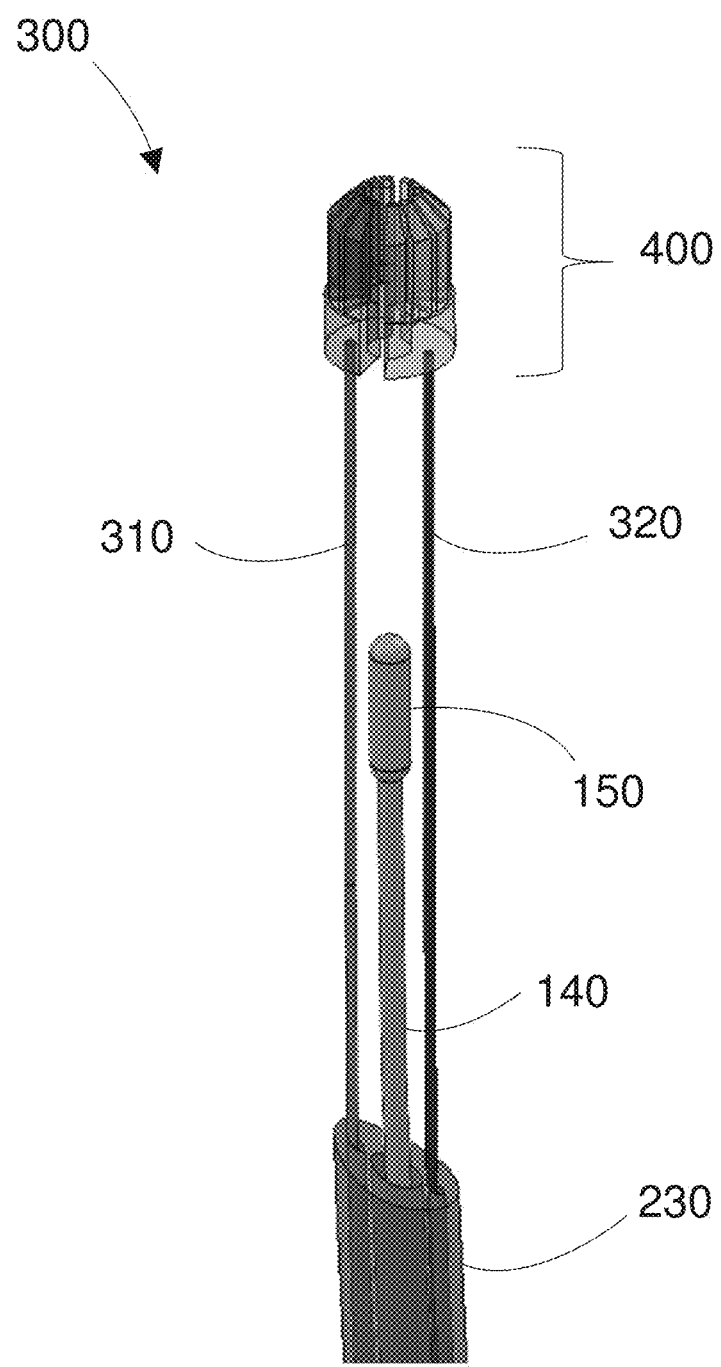
FIG. 3 is an axonometric view of signal transfer means of a transfer tube of the sensing apparatus of FIG. 2.

FIG. 3 shows an axonometric view of the signal transfer means 300 arranged at or near the second end of the transfer tube 230. The signal transfer means 300 comprises a first optical fibre 310, a second optical fibre 320 and light transfer means 400. The light transfer means 400 may also be referred to as a light transferer, light transfer equipment or light transfer apparatus. The first optical fibre 310 and the second optical fibre 320 are embedded in opposing sides of the wall of the transfer tube 230 and (although not shown) extend along the length of the transfer tube 230. That is, the first and second optical fibres 310, 320 are each embedded in the wall of the transfer tube 230 and are orientated at approximately 180 degrees to each other. In other examples, the first 310 and second 320 optical fibres may be orientated differently within the transfer tube 230.

The first and second optical fibres 310, 320 are each coupled, or connected, with the light transfer means 400. In this example, the first and second optical fibres 310, 320 are inserted into holes formed in the light transfer means 400 and secured there using glue, for example. However, the first and second optical fibres 310, 320 may be connected with the light transfer means 400 in any way that will occur to the skilled person provided light may still pass between each of the optical fibres 310, 320 and the light transfer means 400. The light transfer means 400 will be described in more detail in relation to FIG. 4.

Figure 4:
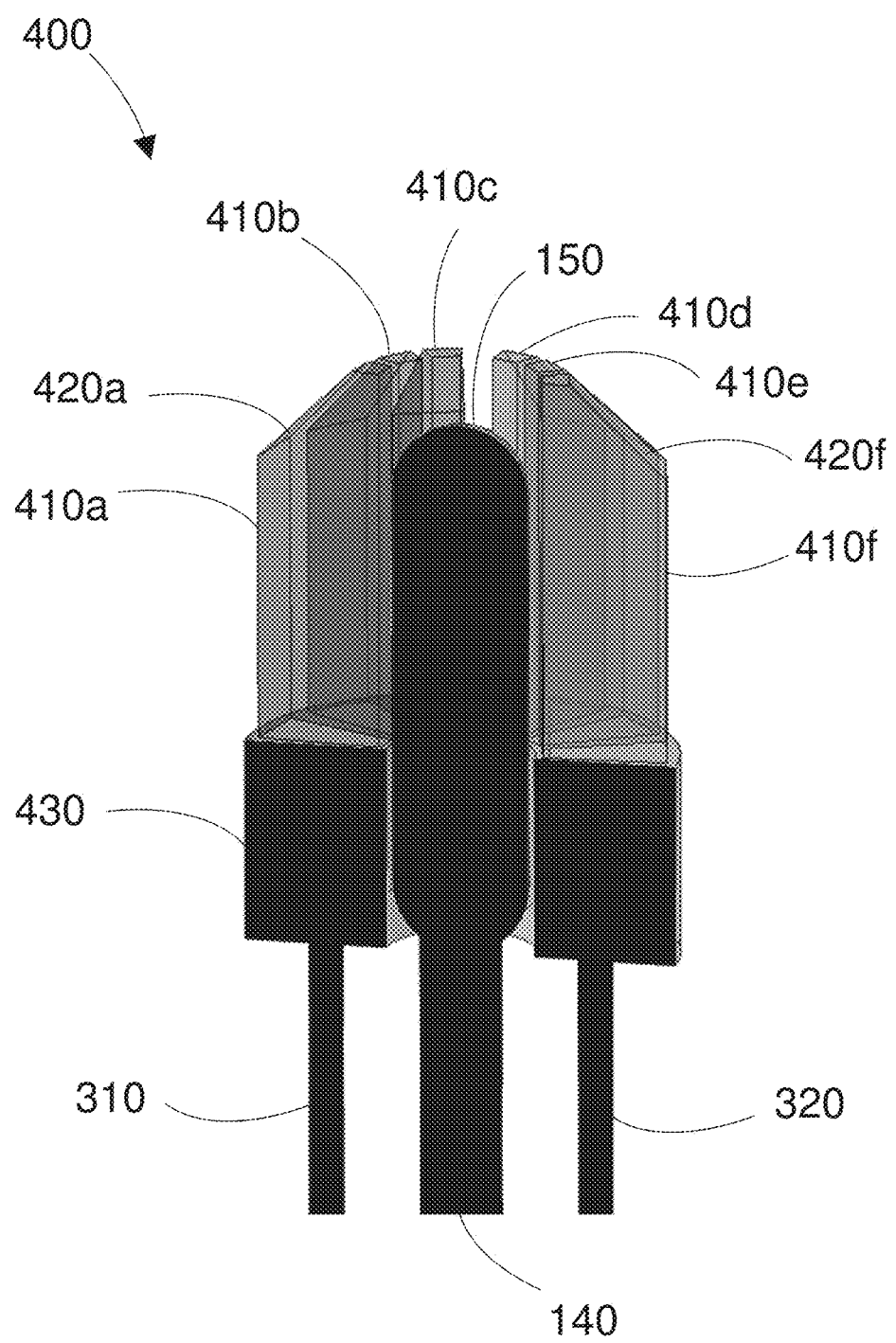
FIG. 4 is an axonometric sectional view of light transfer means of the signal transfer means of FIG. 3.

FIG. 4 is an axonometric sectional view of the light transfer means 400. The light transfer means 400 comprises at least two light transfer elements. The light transfer elements may be referred to as light directing elements, or prisms, and these terms will be used interchangeably herein. In this example, the at least two light transfer elements comprise various prisms. As FIG. 4 shows a sectional view of the light transfer means 400, only a couple of prisms 410*a-f* are shown.

Each light directing element 410*a-f* is configured to direct light. A first arrangement of light directing elements comprises one or more of the light directing elements 410 *d-f* coupled and/or connected with the first optical fibre 310. A second arrangement of light directing elements comprises one or more of the light directing elements 410*a-c* coupled and/or connected with the second optical fibre 320. Each of the second arrangement of light directing elements 410*d-f* is configured to receive light from the second optical fibre 320, and direct the light across the inner channel, or passageway, of the transfer tube 230 and toward the first arrangement of light directing elements 410*a-c*. Each of the first arrangement of light directing elements 410*a-c* is configured to receive light directed across the inner channel of the transfer tube 230, and direct that light to the first optical fibre 310. The light directing elements 410*a-f* may comprise light reflecting, or directing, surfaces 420*a-f*, and may be configured and positioned to direct light via these surfaces 420*a-f*.

The particular implementation of the light directing elements 410*a-f* depicted in FIG. 4 will now be described. Each of the prisms 410*a-f* has a base. The base of each prism 410*a-f* extends approximately between the outer diameter of the transfer tube 230 and the inner diameter of the transfer tube 230. In other words, the base of each prism 410*a-f* extends approximately between an outer surface of the transfer tube 230 and an inner surface of the transfer tube 230. The base of each prism 410*a-f* interfaces with both the second end of transfer tube 230 and the first and second optical fibres 310, 320 embedded in the transfer tube 230 wall. In this way, the prisms 410*a-f* may be considered as being arranged at or near the second end of the transfer tube 230. The prisms 410*a-f* are approximately equally distributed around the inner diameter of the transfer tube 230. The inner diameter of the transfer tube 230 is defined as being the diameter of the passage way provided inside the transfer tube 230. That is, the inner diameter of the transfer tube 230 is the outer diameter of the transfer tube 230 minus the thickness of the wall of the transfer tube 230.

The bases of the prisms 410a-f interface and are connected with the transfer tube 230 body using any suitable securing means. For example, the bases of the prisms 410a-f may be connected with the transfer tube 230 body using an adhesive or a mechanical clamp or fixing.

In other examples, there is no direct physical attachment between the bases of the prisms 410a-f and the transfer tube 230 body. Instead, in such examples, the prisms 410a-f are attached to the transfer tube 230 body via the connection between the first and second optical fibres 310, 320 only.

The prisms will herein be referred to as light directing elements. Light directing elements 410a-f are thus shown in FIG. 4.

Each of the plurality of light directing elements 410a-f extends—that is, has a length—in a direction parallel to the axis of the transfer tube 230. The base of each of the plurality of light directing elements 410a-f is substantially isosceles trapezoid shaped. This isosceles trapezoid shape is maintained—that is, extruded—for around three quarters of the total length of each of the plurality of light directing elements 410a-f. The isosceles trapezoid shape then tapers to a point having an approximately square cross section. This point is positioned proximate to the inner diameter of the transfer tube 230. The cable 140 and the article 150 may thus still travel through both the transfer tube 230 and the centre of the light directing elements 410a-f.

The tapering of the light directing elements 410a-f results in each of the light directing elements 410a-f having a reflecting surface 420a,f orientated at approximately 45 degrees to the axis of the transfer tube 310. The orientation of the reflecting surfaces 420a,f of the light directing elements 410a-f has a specific purpose in the functioning of the light directing elements 410a-f as described in more detail below. Two reflecting surfaces 420a,f are shown in FIG. 4.

As set out above, the light transfer means 400 interfaces with the first and second optical fibres 310, 320. In more detail, as shown in FIG. 4, in this arrangement, the first and second optical fibres 310, 320 terminate near the end of the transfer tube 230 which interfaces with the light transfer means 400—that is, near the second end of the transfer tube 230. Close to the point of termination—that is, close to the second end of the transfer tube 230—the cross-sectional areas of the first and second optical fibres increase. The first and second optical fibres 310, 320 each have a substantially circular cross-section. The diameters of the first and second 310, 320 optical fibres are, for the majority of the length of the transfer tube 230, approximately one quarter of the thickness of the transfer tube 230 wall. Due to the relative size of the first and second optical fibres 310, 320 and the outer diameter of the transfer tube 230, not all of the light directing elements 410a-f interface directly—for example, are in direct contact with—one of the first or second optical fibres 310, 320.

In other examples, the cross-sectional areas of the first and second 310, 320 optical fibres may: be approximately constant along the length of the transfer tube 230; vary along the length of the transfer tube 230; be different to each other at one or more points along the length of the transfer tube 230; have a substantially square or rectangular cross-section; have a triangular cross-section.

In this example, the plurality of light directing elements are formed of glass. In other examples however, the plurality of light directing elements may each or all be made of any material transparent or semi-transparent for the range of optical wave lengths used, such as clear plastic or a glass composite.

Figure 5:
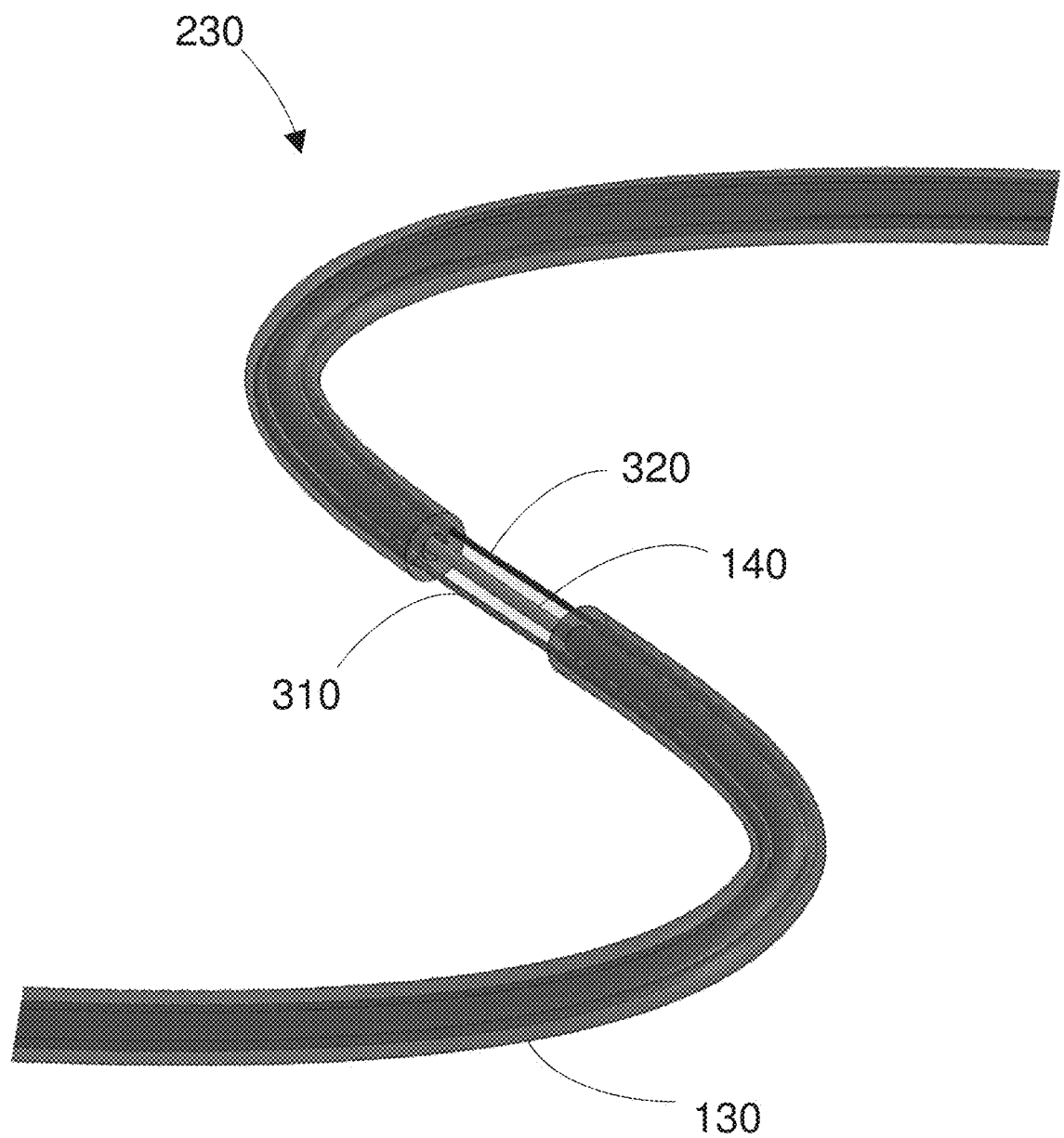
FIG. 5 is an axonometric view of a portion of the transfer tube of the sensing apparatus of FIG. 2.

FIG. 5 shows an axonometric view of a portion of the transfer tube 230. A section of the transfer tube 230 is cut away approximately mid-way along its length to clearly show the internal features of the transfer tube 230. The internal features of the transfer tube 230 include: the first optical fibre 310, the second optical fibre 320, and the internal passageway of the transfer tube 230. As previously described, the first and second optical fibres 310, 320 are each embedded into the wall of the transfer tube 230, extend along the length of the transfer tube 230 (and thus are parallel to the axis of the transfer tube 230), and are orientated approximately 180 degrees from one another. The inner diameter of the transfer tube 230, which defines the outer diameter of the internal passageway, is approximately half of the outer diameter of the transfer tube 230. Also shown in FIG. 5 is the cable 140 running through the internal passageway. The diameter of the cable 140 is sufficiently smaller than that of the internal diameter of the transfer tube 230 such that the cable 140 and article 150 may easily travel through the transfer tube 230 without catching or suffering from burdensome amounts of friction on the transfer tube 230 inner wall.

In FIG. 5, a section of the transfer tube is shown, which also includes metal support wires, which are used to strengthen the transfer tube.

Figure 6:
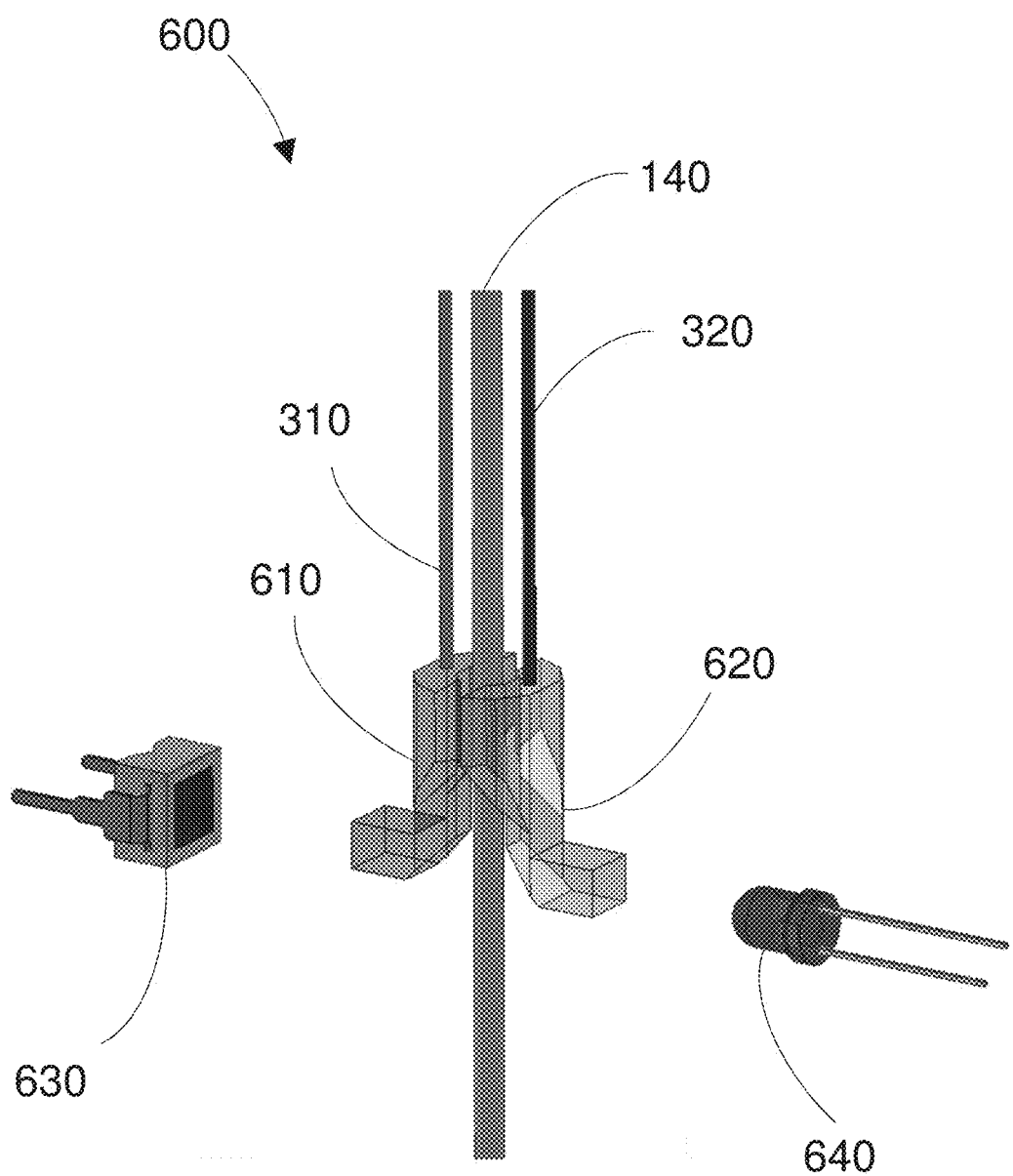
FIG. 6 is a part-exploded axonometric view of further light transfer means of the sensing apparatus of FIG. 2.

FIG. 6 shows a part-exploded axonometric view of the sensor system 600 of FIG. 2.

The sensor system 600 includes further light transfer means 610, 620, a light source 640, and a sensing means 630.

The further light transfer means may also be referred to as a further light transferer, further light transfer equipment or further light transfer apparatus. The sensing means 630 may also be referred to as a sensor, or light sensing or detection means. The sensing means 630 may be, for example, a camera.

As discussed above, the sensor system 600 interfaces with the first end of the transfer tube 230. The transfer tube 230 thus interfaces at its second end with the signal transfer means 300 and at its first end with the sensor system 600. The sensor system may be located within the afterloader 110.

The further light transfer means is configured to receive light from the light source 640, and direct it to, along, or down, the second optical fibre 320. The further light transfer means is also configured to receive light from the first optical fibre 310, and direct it toward the sensor 630. As with the light transfer means 400, the further light transfer comprises one or more light directing elements 610, 620, and these light directing elements 610, 620 may comprise light reflecting, or directing, surfaces, and may be configured and positioned to direct light via these surfaces.

In more detail, and with reference to the implementation depicted in FIG. 6, the further light transfer means 610, 620 includes a first further light directing element 610 and a second further light directing element 620. Each of the first 610 and second 620 further light directing elements has a first and a second end. The first end of the first further light directing element 610 interfaces with, and/or couples with, the first optical fibre 310. The second end of the first further light directing element 620 interfaces with, and/or couples with, the sensor 630. Meanwhile, the first end of the second further light directing element 620 interfaces with, and/or couples with, the second optical fibre 320. The second end of the second further light directing element 620 interfaces with, and/or couples with, the light source 640.

The first and second further light directing elements 610, 620 are, in this example, identically shaped. In other examples, the first and second further light directing elements 610, 620 may not be identical. Each of the first and second further light directing elements 610, 620 is approximately shaped, and operates in the manner of, a periscope cut in half mid-way along its length. The first and second further light directing elements 610, 620 thus each are predominantly formed of two sections: a first section and a second section. The first section is approximately square in cross-section and extends—that is, has length—in a direction parallel with the axis of the transfer tube 230 until it tapers at one end into the second section. The second section, which is likewise also approximately square in cross-section, extends—that is, has length—in a direction perpendicular to the axis of the transfer tube 230. Due to the tapering of the first section as it joins with the second section, a further reflecting surface is formed. The further reflecting surface is orientated at approximately 45 degrees to the axis of the transfer tube 230.

The first section of each of the first and second further light directing elements 610, 620 interfaces with the first and second optical fibres 310, 320, respectively. Meanwhile, the second section of each of the first and second further light directing elements 610, 620 interfaces with the sensor 630 and light source 640, respectively.

The first and second further light directing elements 610, 620 are arranged such that they each of their second sections is oriented away from the axis of the transfer tube 230. As a result, the first and second further light directing elements 610, 620 are in a mirror image arrangement about the plane which dissects the axis of the transfer tube 230 and which is disposed between the first and second optical fibres 310, 320.

The first and second further light directing elements 610, 620 are both sized and arranged such that a passageway between the first and second further light directing elements 610, 620 is provided which has substantially the same diameter as the internal diameter of the transfer tube 230. As a result, as shown in FIG. 6, in use the cable 140 may pass between the first and second further light directing elements 610, 620 and into the transfer tube 230.

In the present disclosure, the term interface(s) is taken to mean arranged to exchange signals in a one or two-way relationship. Such signals may be light signals.

In this example, the first and second further light directing elements 610, 620 are formed of glass. In other examples however, either or both of the first and second further light directing elements 610, 620 may be made of any transparent or semi-transparent material, such as clear plastic or a glass composite, similar to the light directing elements in FIG. 4.

Operation

The operation of the sensing apparatus 200 will now be described in reference to FIG. 13.

Figure 13:
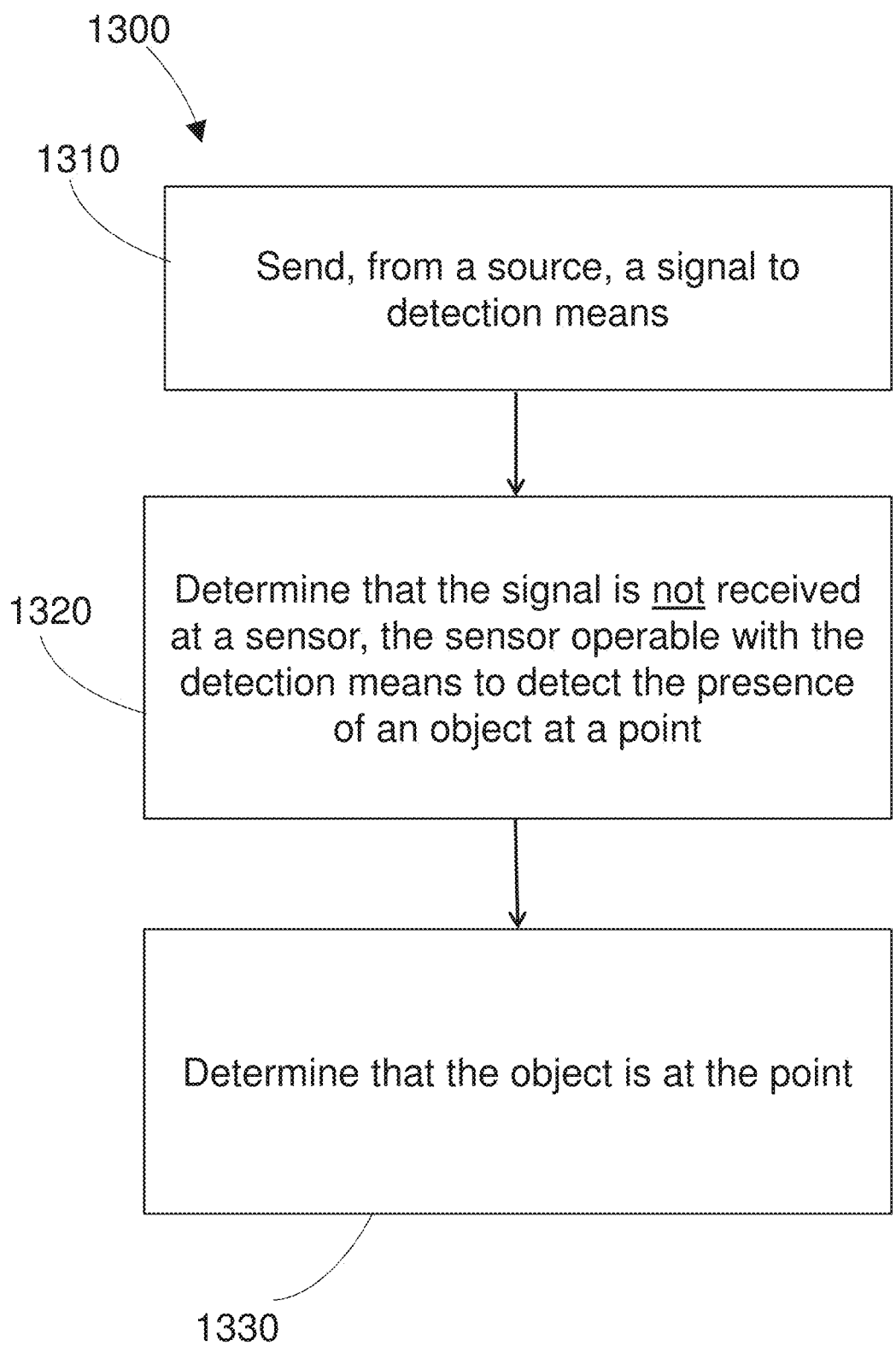
FIG. 13 is a flow diagram of a method of determining the presence of an article, at a point along a transfer tube.

FIG. 13 shows a method 1300 for determining whether or not an article, such as a radioactive source, is at a point in, for example, the guide tube 230.

The method includes, at step 1310, sending, from the source 640, a signal to the signal transfer means 300.

In this example, as the source 640 is a light source 640, the method involves sending, from the light source 640, a light signal to the signal transfer means 300. The signal transfer means 300 may be referred to as a light transfer means. In more detail, due to the interface between the light source 640 and the second further light directing element 620, the light signal is transmitted into the second section of the second further light directing element 620. The light signal travels approximately along the length of the second section until it impinges upon the further reflecting surface of the second further light directing element 620. As previously discussed, the further reflecting surface is orientated at approximately 45 degrees to the axis of the transfer tube 230 and thus, upon impinging upon the further reflecting surface, the light signal is reflected by approximately 90 degrees. Accordingly, the light signal then travels approximately along the length of the first section of the second further light directing element 620 until it impinges upon the interface of the second section with the second optical fibre 320. At this point, the light signal is transmitted into the second optical fibre 320 and the light signal travels along the length of the second optical fibre 320 and thus along the length of the transfer tube 230 until the light signal reaches the other end of the second optical fibre 320; that is, the end of the second optical fibre which interfaces with one or more of the light directing elements 410a-f.

On reaching that end of the second optical fibre 310 which interfaces with one or more of the light directing elements 410a-f, the light signal transfers into those one or more light directing elements 410a-f. In other words, the light signal transfers into the second arrangement of light directing elements 420d-f i.e. the ones of the plurality of light directing elements 410a-f which interface directly with the second optical fibre 310.

The light signal then travels through each of those ones of the one or more light directing elements 410a-f in a direction approximately parallel to the axis of the transfer tube 230 until the light signal impinges upon the respective reflecting surface 420a,f. As previously discussed, each reflecting surface 420a,f is orientated at approximately 45 degrees to the axis of the transfer tube 230 and thus, upon impinging upon the respective reflecting surface 420a,f, the light signal is reflected by approximately 90 degrees.

The light signal is then transmitted approximately across the diameter of the transfer tube 230—that is, approximately across the centre of the passageway formed in the transfer tube 230. The light signal is thus transmitted towards the first arrangement of light directing elements 410a-c. In other words, the light signal is transmitted towards an opposite one of the plurality of light directing elements 410a-f.

If there is no obstruction to the light signal transmitted across the passageway formed in the transfer tube 230, such as an article, the light signal successfully reaches the opposite one of the plurality of light directing elements 410a-f and is collected by it. In this case, the light signal continues travelling in the opposite one of the plurality of light directing elements 410a-f in a direction substantially parallel with the diameter of the transfer tube 230 until the light signal impinges upon the reflecting surface 420a,f of the light directing element. As previously described, the light signal is then reflected by the respective reflecting surface 420a,f by approximately 90 degrees. As a result, the light signal is then transmitted along the length of the respective light directing element 410a-f until the light signal impinges upon the interface with the first optical fibre 310.

On impinging the interface with the first optical fibre 310, the light signal is transferred into the first optical fibre 310 and is transmitted along the length of the first optical fibre 310, and thus transfer tube 230, towards the sensing means 600.

When the light signal reaches the interface of the first optical fibre 310 with the sensing system 600, the light signal is transferred into the first section of the first further light directing element 610. The light signal travels approximately along the length of the first section in a direction approximately parallel with the axis of the transfer tube 230 until it impinges upon the further reflecting surface of the first further light directing element 610. As previously discussed, the further reflecting surface is orientated at approximately 45 degrees to the axis of the transfer tube 230 and thus, upon impinging upon the further reflecting surface, the light signal is reflected by approximately 90 degrees. Accordingly, the light signal then travels approximately along the length of the second section of the first further light directing element 610 until it impinges upon the interface of the first section with the sensor 630. At this point, the light signal is detected by the sensor 630.

When the light signal is sensed or detected by the sensor 630, it can be concluded—by, for example, control means communicatively coupled with the sensor 630—that there is no obstruction or object present in the passageway of the transfer tube 230 at the point along the length of the transfer tube 230 of the plurality of light directing elements 410*a-f*. This is because, were an obstruction or object present at that point, no light signal would be transferred between the second 320 and first 310 optical fibres, and thus the light signal originally emitted by the light source 640 would not be detected subsequently by the sensor 630.

In contrast, if the light signal transmitted across the passageway formed in the transfer tube 230 is obstructed, for example, by the presence of an object in the passageway, the light signal does not successfully reach the opposite one of the plurality of light directing elements 410*a-f* and is not collected by it. As a result, the light signal does not transfer into the first optical fibre 310, nor the first further light directing element 610, and thus no light signal is detected by the sensor 630.

In this latter case, the method 1300 includes, at step 1320, determining that the signal (in this example, the light signal), is not received at the sensor 630, the sensor 630 being operable with the signal transfer means 300 to detect the presence of an object at a point. In this example, the point is the point along the length of the transfer tube 230 where the plurality of light directing elements 410*a-f* are arranged.

The method 1300 then progresses to step 1330 where it is determined that an object is at the point. The object may be a check cable or a radioactive source, for example, furthermore called article.

In summary therefore, the sensing apparatus 200 can function in the described way to, ultimately, more accurately position the article 250 inside the applicator 170. This is because, when the article 250 is determined by the sensing apparatus 200 as being at the point in the transfer tube 230, this point can be set as the zero reference point and the progression of the article 250 into the applicator 170 can be controlled relative to this zero reference point. As a result, variations in the set up of the transfer tube 230 are accounted for since the travel path of the article 250 through the transfer tube 230 up to the zero reference point is unimportant and has no effect on the ultimate accuracy of the positioning of the article 250 in the applicator 170 as this is only calculated and executed based on the zero reference point.

The operation of the sensing apparatus 200 to control the position of an object, such as the article 150 will now be described in reference to FIG. 14. The steps of FIG. 14 lead on from those of FIG. 13.

Figure 14:
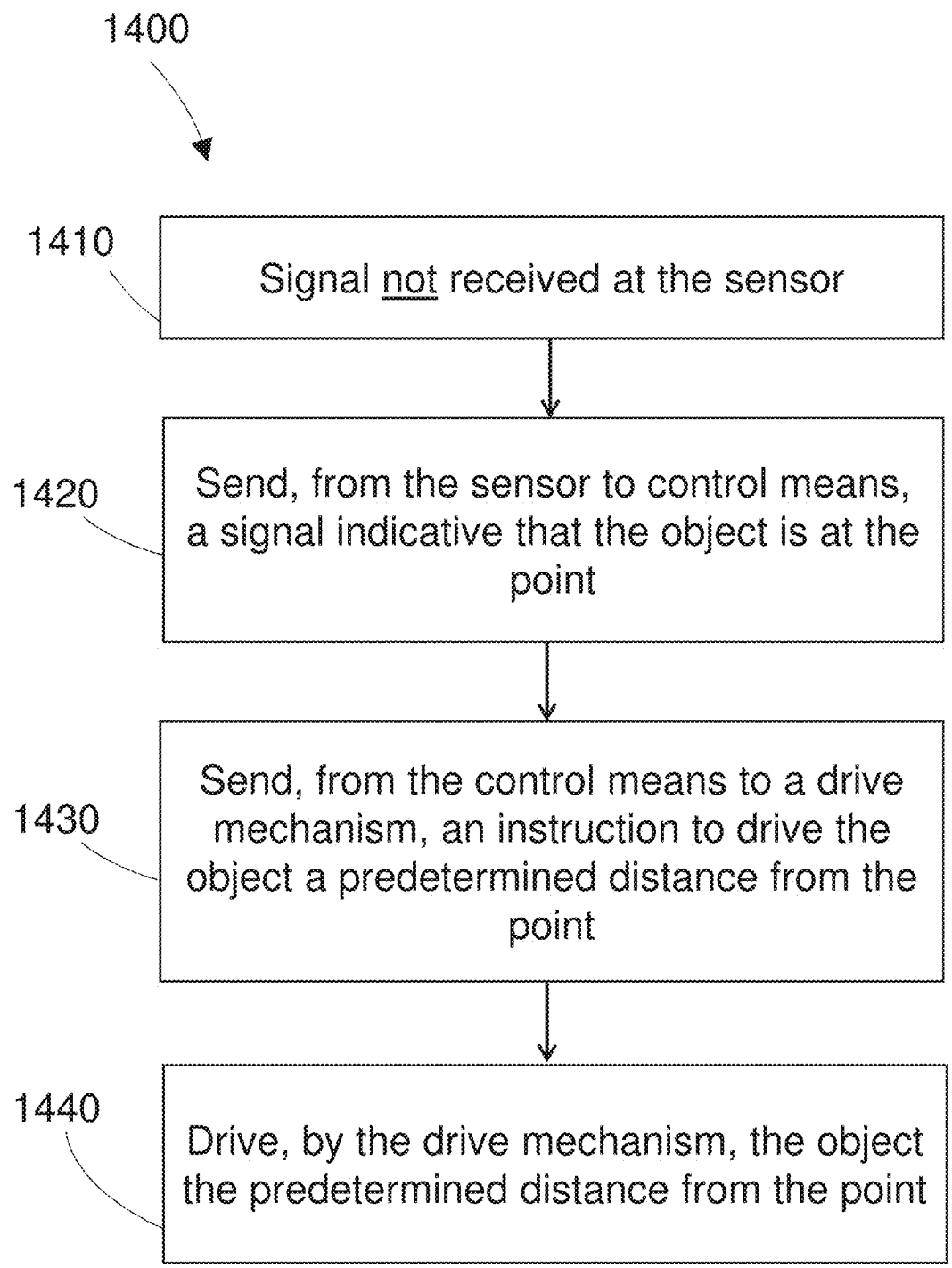
FIG. 14 is a flow diagram of a method of driving the article a predetermined distance from the point along the transfer tube.

FIG. 14 shows a method 1400 which includes, at step 1410, the signal not being received at the sensor. In this case, the signal is the light signal (as previously described) and the sensor is the sensor 630 shown in FIG. 6.

At step 1420, the method includes sending, from the sensor to control means, a signal indicating that the object is at the point. In this example, the sensor is the sensor 630 shown in FIG. 6 and the point is the point along the length of the transfer tube 230 where the plurality of light directing elements 410*a-f* are arranged. Thus, in this example, the point is at the second end of the transfer tube 230 (i.e. the end of the transfer tube 230 arranged to connect with the applicator 170).

Next, at step 1430, the method includes sending, from the control means to a drive mechanism, an instruction to drive the object a predetermined distance from the point. In this example, the drive mechanism is the drive mechanism 120 comprised in the afterloader 110 as described in relation to FIG. 1. Thus, in this example, the method includes sending, to the drive mechanism 120, an instruction to drive the object, such as article 150, a predetermined distance from the second end of the transfer tube 230 (i.e. the end of the transfer tube 230 arranged to connect with the applicator 170). Accordingly, in this example, the instruction is an instruction to drive the article 150 a predetermined distance into the applicator 170 from the transfer tube 230.

In some arrangements, the control means are housed in the afterloader 110. In other arrangements, the control means are housed external to the afterloader 110. The control means are, regardless of physical location, communicatively coupled with the sensor and the drive mechanism.

Next, at step 1440, the method includes driving, by the drive mechanism, the object the predetermined distance from the point. In this example therefore, the method includes driving, by the drive mechanism 120, the article 170 the predetermined distance from the second end of the transfer tube 230 (and thus into the applicator 170).

In this way, the point can be considered as a zero reference point. This is because the predetermined distance is measured from this zero reference point.

Advantages

Advantageously, the described sensing apparatus 200 and corresponding methods 1300, 1400 deliver a key benefit that the position of an object, such as a check cable or radioactive source, at a certain point along the length of the transfer tube 230 can be accurately detected. This means that this point can be set as a zero reference point and the object driven from the transfer tube 230 into an applicator 170 based on a calculation from that point. As a result, variations in the practical arrangement of the transfer tube 230 before the zero reference point do not affect the accuracy of the ultimate positioning of the object in the applicator 170. Variations in the practical arrangement of the transfer tube 230 can include variations in, for example: the ambient room temperature in which the transfer tube 230 is being used; the temperature of the transfer tube 230; the arrangement in space of the transfer tube 230 (such as whether the transfer tube 230 is perfectly straight, or perhaps quite curvy). Accordingly, the overall accuracy of positioning the article inside an applicator 170 and thus human body is increased.

Furthermore, some advantages specific to the sensing apparatus 200 are that:

Disclosed herein is a sensing apparatus for sensing the presence of the article at a point along a transfer tube. As noted above, the point may be where the light transfer means 400 and light directing elements 410*a-f* are positioned. Because the point is in the transfer tube rather than in the afterloader, any system tolerances built up in the tube before that point, e.g. due to snaking of the cable or transfer tube length variations, are accounted for.

In a preferred implementation, the point is located near to the second end of the transfer tube—that is, the end of the transfer tube which is connected, or connectable, with the applicator. Overall, the closer the point is to the second end of the transfer tube, the higher the accuracy of the ultimate positioning of the article in the applicator. This is because a larger proportion of the system tolerances that build up in the tube are accounted for. Put another way, the advantageous effect described in the preceding paragraph is increased when the point is nearer the second end of the transfer tube.

In a yet further preferred implementation, the point is located at the extreme second end of the transfer tube 230 arranged for connection with the applicator 170. In this implementation, the accuracy of the ultimate positioning of the article in the applicator 170 is entirely independent of variations in the practical arrangement of the transfer tube 230. Put another way, the accuracy of the ultimate positioning of the article in the applicator 170 is entirely independent of the distance the article must travel to reach the second end of the transfer tube 230, and thus the zero reference point. Accordingly, a highly accurate approach for positioning the article in the applicator is provided.

The use of several light directing elements 410*a-f* (for example, in the sensing apparatus 200, various light directing elements are used) provides a simple manufacturing procedure. This is because, due to their number, ranging from four to six or even higher numbers precise alignment of the light directing elements 410*a-f* with the first 310 and second 320 optical fibres is not necessary. This is because the likelihood of either of the first 310 or second 320 optical fibres not being interfaced with at least one of the light directing elements 410*a-f* is low. Accordingly, the light directing elements 410*a-f* need not be precisely arranged around the circumference of the transfer tube 230 and so the manufacturing procedure may be simplified.

Regardless of their number, the shape of the light directing elements 410*a-f* is such that they are invulnerable to misalignment with the first 310 and second 320 optical fibres 310, 320. This is due to the bases of the light directing elements 410*a-f* extending from approximately the inner diameter of the transfer tube 230 to the approximately the outer diameter of the transfer tube 230. As a result, the light directing elements 410*a-f* each have a relatively large contact surface for possible interfacing with the first 310 or 320 second optical fibre.

Alternative Arrangements

The above implementations have been described by way of example only, and the described implementations and arrangements are to be considered in all respects only as illustrative and not restrictive. It will be appreciated that variations of the described implementations and arrangements may be made without departing from the scope of the invention.

The first 310 and second 320 optical fibres may each comprise a single optical fibre filament or a plurality of optical fibre filaments. For example, each of the first 310 and second 320 optical fibres may comprise a bundle of optical fibre filaments and/or be comprised of a string of interfacing optical fibres. Each of the first 310 and second 320 optical fibres may be formed of any transparent material, such as silica or plastic. Each of the first 310 and second 320 optical fibres may be flexible or rigid. When one or both of the first 310 and second 320 optical fibres is rigid, the rigid optical fibre(s) may advantageously provide structural support to the transfer tube 230.

The transfer tube 230 may optionally additionally comprise one or more support wires. The one or more support wires may be embedded in the wall of the transfer tube 230. For example, the one or more support wires may be embedded in a similar fashion to the first 310 and second 320 optical fibres. In a particular arrangement, there may be two support wires: a first and a second support wire. Each of the first and second support wires may extend substantially along the length of the transfer tube 230. The first and second support wires may be oriented around 180 degrees from each other in the transfer tube 230 wall. That is, be disposed opposite each other in the transfer tube 230 wall. Accordingly, the first and second support wires may each be oriented around 90 degrees from both the first 310 and second 320 optical fibres. The presence of support wires may help avoid significant kinks in the transfer tube 230 which has numerous technical advantages, including: reducing friction between the transfer tube 230 and the cable 140 and/or article 150 passing through the transfer tube 230, which can help protect the cable 140, article 150 and transfer tube 230 from degradation; and reducing the likelihood that the cable 140 and/or article 150 gets stuck in the transfer tube 230.

FIG. 5 shows the layout of the transfer tube featuring both optical and mechanical wires.

The light source 640 may be any kind of signal source. For example, the source 640 may be an LED light source arranged to emit light of a wavelength in the visible light spectrum. Alternatively, or additionally, the source 640 may instead be a light source arranged to emit light of a different optical wavelength or parts of the infrared spectrum. Alternatively, or additionally, the source 640 may instead be an ultraviolet light source arranged to emit light of a wavelength in the ultraviolet spectrum. The sensor 630 may thus be any sensor suitable for detecting light of the type emitted by the source 640. For example, the sensor 630 may be configured to detect light in the visible light spectrum and/or infrared spectrum and/or ultraviolet spectrum. The sensor 630 may be a camera or camera apparatus. The camera apparatus may comprise a wide angle lens so as to allow the camera arrangement to detect light received from a plurality of optical fibres.

Although the light source 640 and sensor 630 have thus far been described as being distinct apparatus, one or both of the light source 640 and sensor 630 may be a transceiver unit. In particular, both the light source 640 and sensor 630 may be a single transceiver unit. Where modifications are made to the arrangement of the light source 640 and sensor 630, modifications to the design and/or arrangement of the further light directing elements 610, 620 may be required, as will occur to the skilled person.

Multiposition Sensing

Figure 7:
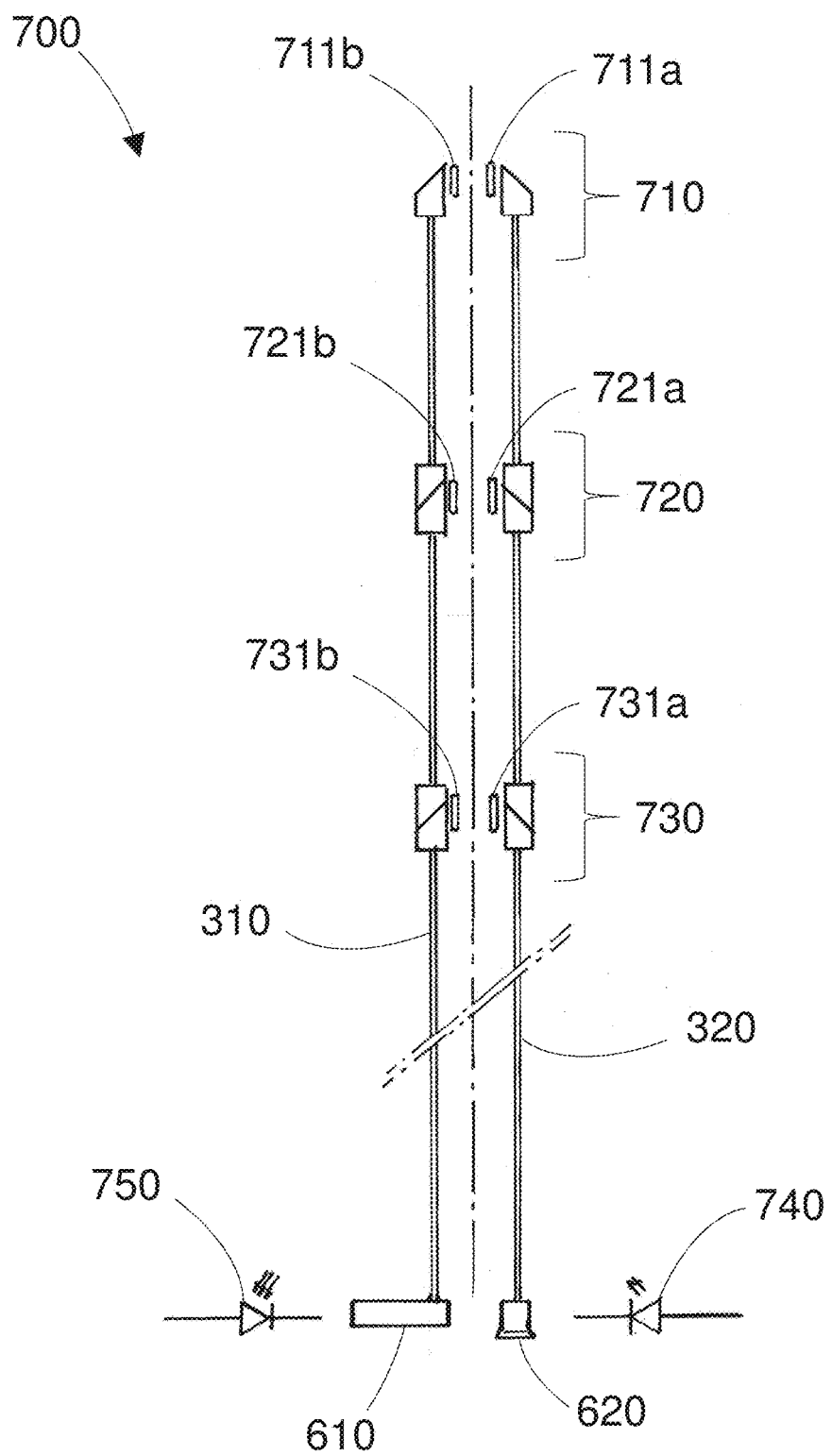
FIG. 7 is a sectional view of a sensing apparatus that is a second implementation.

FIG. 7 shows a sectional view of a sensing apparatus 700 that is a second implementation of the present disclosure.

A difference between the sensing apparatus 700 of this second implementation and the sensing apparatus 200 of the first implementation is that the sensing apparatus 700 has light directing elements distributed at a plurality of points along the length of the sensing apparatus 700, rather than at a single point (as in the sensing apparatus 200 shown in FIG. 2). As a result, the sensing apparatus 700 is arranged to detect the presence of an object, such as cable 140 or any variation of article 150, at a plurality of points along the length of the sensing apparatus 700, rather than at a single point.

In overview, electromagnetic radiation of different wave length is emitted by a light source 740 and directed down a second optical fibre 320. The light may be comprised of the different frequencies, or light of differing frequencies may be emitted at different times. Via a suitable arrangement of wave length (color) filters and/or beam splitters, it is possible to make use of a plurality of light transfer means, each positioned at different points along the transfer tube and/or applicator unit and each configured to transfer one of the wave length of light to the first optical fibre, to detect the presence of an object in the transfer tube at each of the different points along the applicator unit and transfer tube.

In an example, light comprising two ranges of wavelengths is directed along the second optical fibre. A first light transfer means is configured to interact with the first and second ranges of wavelengths in a different manner. The first light transfer means is configured to pass the second range of wavelengths such that the second range of wavelengths continue to travel along the second optical fibre. The first light transfer means is also configured to transfer the first range of wavelengths of light across the passageway of the transfer tube and direct it down the first optical fibre to be sensed by the sensor 750. A second light transfer means positioned further downstream along the transfer tube is configured to transfer the second range of wavelengths of light across the passageway of the transfer tube and direct it down the first optical fibre to be sensed by the sensor 750.

In an example, light comprising two frequencies is directed along optical fibre 320.

A first light transfer means 730 is configured to split the light beam into two directions: both substantially straight ahead and substantially 90 degrees bent. The bent light is filtered by filter 731A and the second frequency is removed form this part of the light beam. At the second light transfer mean 720 or 710, the beam is (partly or not) bended substantially 90 degrees again. This beam is also filtered, but here frequency one is removed.

This creates two sensitive areas where light transfer 730 is sensitive for frequency one, and light transfer 710 or 720 is sensitive for frequency two.

An article obstructing light transfer 730, obscures frequency one, which the multi-color or multi-frequency detector 750 is able to distinguish from frequency two, and so detect the presence of the article at point 730.

An article obstructing for example light transfer 710, obscures frequency two, which the multi-color or multi-frequency detector 750 is able to distinguish from frequency one, and so detect the presence of the article at point 710.

A multitude of beam splitting elements and frequency filters, is therefore able to detect articles at a multitude of locations independently.

In more detail, the sensing apparatus 700 includes a first optical fibre 310 and a second optical fibre 320. As before, the first and second optical fibres 310, 320 extend at least along the length of the transfer tube and, in some examples, may extend beyond the transfer tube as will be described in reference to FIG. 8. The arrangement and configuration of the first and second 310, 320 optical fibres may be substantially as described in relation to the sensing apparatus 200.

The first and second optical fibres 310, 320 each comprise a first end and a second end. The first ends of the first and second optical fibres 310, 320 interface with the sensor system, and in particular with first 610 and second 620 further light directing elements respectively. The first and second optical fibres 310, 320 interface with the respective one of the first and second further light directing elements 610, 620 in substantially the same way as described in relation to the sensing apparatus 200, particularly in relation to FIG. 6. Furthermore, signals may pass between each of the first and second optical fibres 310, 320 and the first and second further light directing elements 610, 620 respectively in substantially the same manner as described in relation to the sensing apparatus 200.

The sensing apparatus 700 further includes a multiple-frequency light source 740 and a multi-frequency sensor 750. The multiple-frequency light source 740 is configured to emit light comprising wavelength(s) corresponding to at least three different wavelengths, for example three different colours in the visible colour spectrum. The multi-frequency light source 740 may simple be a broadband source such as a light source configured to emit white light. The multi-frequency sensor 750 is correspondingly configured to detect the particular wavelength(s) corresponding to the at least three different wavelengths, e.g. the three different colours.

The sensing apparatus 700 further comprises a first, second and third light transfer means each comprising a first 710, second 720 and third 730 plurality of light directing elements respectively. The first plurality of light directing elements 710 interface the second ends of first and second 310, 320 optical fibres. The second plurality of light directing elements 720 interface the first and second 310, 320 optical fibres at a first distance from the second ends of the first and second 310, 320 optical fibres. The third plurality of light directing elements 730 interface the first and second 310, 320 optical fibres at a second distance from the second ends of the first and second 310, 320 optical fibres. The second distance may be approximately double the first distance. In this arrangement, both the second 720 and third 730 plurality of light directing elements interface the first and second 310, 320 optical fibres at a position closer to the second end of the first and second optical fibres 310, 320 than the first end of the first and second optical fibres 310, 320.

The first plurality of light directing elements 710 is substantially the same (both physically and in function) as the plurality of light directing elements 410a-f comprised in the sensing apparatus 200. The sensing apparatus 700 additionally comprises however first 711a and second 711b colour filters. The first 711a and second 711b colour filters are substantially the same and both permit only light of a first wavelength or wavelength range to pass through them. The first colour filter 711a is approximately aligned with the ones of the first plurality of light directing elements 710 which, in use, will absorb light from the second optical fibre 320. The second colour filter 711b is approximately aligned with the ones of the first plurality of light directing elements 710 which, in use, will transmit light to the first optical fibre 310.

The second 720 and third 730 plurality of light directing elements are substantially the same. Each of the elements in the second 720 and third 730 pluralities of light directing elements is approximately cuboidal in shape, the cuboid having a length, a width and a depth. The length of the cuboid is greater than its width or depth. Each of the elements in the second 720 and third 730 pluralities of light directing elements is oriented in space such that its length is approximately parallel with the axis of the transfer tube 230. A proportional reflecting surface is provided approximately mid-way along the length of each of the elements in the second 720 and third 730 pluralities of light directing elements. The proportional reflecting surface is a slanted surface arranged at approximately 45 degrees to the axis of the transfer tube 230.

The sensing apparatus 700 additionally comprises third 721a and fourth 721b colour filters. The third 721a and fourth 721b colour filters are substantially the same and both permit only light of a second wavelength or wavelength range to pass through them. The third colour filter 721a is approximately aligned with the ones of the second plurality of light directing elements 720 which, in use, will absorb light from the second optical fibre 320. The third colour filter 721b is approximately aligned with the ones of the second plurality of light directing elements 720 which, in use, will transmit light to the first optical fibre 310.

Further still, the sensing apparatus 700 additionally comprises fifth 731a and sixth 731b colour filters. The fifth 731a and sixth 731b colour filters are substantially the same and both only permit light of a third wavelength or wavelength range to pass through them. The fifth colour filter 731a is approximately aligned with the ones of the third plurality of light directing elements 730 which, in use, will absorb light from the second optical fibre 320. The sixth colour filter 731b is approximately aligned with the ones of the third plurality of light directing elements 730 which, in use, will transmit light to the first optical fibre 310.

In operation, the multi-frequency light source 740 emits a light signal into the second optical fibres 320 and, in the way described in relation to the sensing apparatus 200, the light signal is transmitted into the second optical fibre 320. The light signal then travels along the second optical fibre 320 until it reaches the third plurality of light directing elements 730. When the light signal reaches the third plurality of light directing elements 730, the light transfers into the one or more of the third plurality of light directing elements 730 which directly interface with the second optical fibre 310. The light signal then transfers along the length of those ones of the light directing elements 730 until the light signal impinges upon the proportional reflecting surface. As previously discussed, each proportional reflecting surface is orientated at approximately 45 degrees to the axis of the transfer tube 230 and thus, upon impinging upon the proportional reflecting surface, a first proportion of the light signal is reflected by approximately 90 degrees. Meanwhile, a second proportion of the light signal is not reflected by the proportional reflecting surface and continues transferring along the length of the light directing element 730. Upon impinging again the second optical fibre 320, this second proportion of the light signal is transmitted into the second optical fibre 320.

Meanwhile, the first proportion of the light signal is transmitted approximately across the diameter of the transfer tube 230—that is, approximately across the centre of the passageway formed in the transfer tube 230. Before the first proportion of the light signal is transmitted across the diameter of the transfer tube 230 however, the first proportion of the light signal must pass through the fifth colour filter 731. As a result, the fifth colour filter 731a only permits light of the third wavelength or wavelength range from the first proportion of the light signal to pass through.

If there is no obstruction to the first proportion of the light signal transmitted across the passageway formed in the transfer tube 230 at the location of the third plurality of light directing elements 230, then the first proportion of the light signal reaches the sixth colour filter 731b. The sixth colour filter 731b removes any remaining light in the first proportion of the light signal which is not of the third wavelength or wavelength range. Subsequently, the first proportion of the light signal transfers into the one or more opposite ones of the third plurality of light directing elements 730. As described in more detail above, the first proportion of the light signal travels in the one or more opposite ones of the third plurality of light directing elements 730 in a direction perpendicular to the axis of the transfer tube 230 until the first proportion of the light signal impinges upon the proportional reflecting surface. As previously discussed, each proportional reflecting surface is orientated at approximately 45 degrees to the axis of the transfer tube 230 and thus, upon impinging upon the proportional reflecting surface, at least some of the first proportion of the light signal is reflected by approximately 90 degrees. As a result, the reflected first proportion of the light signal transfers along the length of the one or more opposite ones of the third plurality of light directing elements 730 in a direction parallel to the axis of the transfer tube 230 until the reflected first proportion of the light signal impinges upon the first optical fibre 310. At this point, the reflected first proportion of the light signal is transmitted into the first optical fibre 310 and travels towards the first further light directing element 610 and multicolor sensor 750. The reflected first proportion of the light signal transfer from the first optical fibre 310 to the first further light directing element 610 and is detected by the multicolor sensor 750 in the way described in relation to the corresponding components in the sensing apparatus 200. On reaching the multicolor sensor 750, the multicolor sensor 750 not only detects generally the presence of the first proportion of the light signal but may, in some arrangements, detect specifically the presence of light in the third wavelength or wavelength range.

Conversely, if there is an obstruction to the first proportion of the light signal transmitted across the passageway formed in the transfer tube 230 at the location of the third plurality of light directing elements 730, then—as the skilled person will understand based upon the description of the sensing apparatus 200—the first proportion of the light signal will not be detected by the multicolor sensor 750. That is, no light in the third wavelength or wavelength range will be detected by the multicolor sensor 750. As result, it may be concluded that there is an obstruction at the location of the third plurality of light directing elements 730.

Returning to the second proportion of the light signal, the second proportion of the light signal continues travelling up the second optical fibre 320 towards the second plurality of light directing elements 720. Upon reaching the second plurality of light directing elements 720, the second plurality of light directing elements 720 function in a substantially similar way as the third plurality of light directing elements 730 such that the second proportion of the light signal is split into approximately a third proportion, which is transmitted across the passageway of the transfer tube 230, and a fourth proportion, which is transmitted back into the second optical fibre 320. The third proportion of the light signal is then filtered by the third 721a and fourth 721b colour filters such that only light in a second wavelength or wavelength range is permitted to pass from the third proportion of the light signal.

If there is no obstruction to the third proportion of the light signal transmitted across the passageway formed in the transfer tube 230 at the location of the second plurality of light directing elements 720, then the third proportion of the light signal will reach the multicolor sensor 750. On reaching the multicolor sensor 750, the multicolor sensor 750 not only detects generally the presence of the third proportion of the light signal but may, in some arrangements, detect specifically the presence of light in the second wavelength or wavelength range. Conversely, if there is an obstruction to the third proportion of the light signal transmitted across the passageway formed in the transfer tube 230 at the location of the second plurality of light directing elements 720, then—as the skilled person will understand based upon the description of the sensing apparatus 200—the third proportion of the light signal will not be detected by the multicolor sensor 750. That is, no light in the second wavelength or wavelength range will be detected by the multicolor sensor 750. As result, it may be concluded that there is an obstruction at the location of the second plurality of light directing elements 720.

Returning to the fourth proportion of the light signal, the fourth proportion of the light signal continues travelling up the second optical fibre 320 towards the first plurality of light directing elements 710. Upon reaching the first plurality of light directing elements 710, the first plurality of light directing elements 710 function in a substantially similar way as the plurality of light directing elements 410*a-f* described in relation to the sensing apparatus 100 such that the fourth proportion of the light signal is transmitted across the passageway of the transfer tube 230. The fourth proportion of the light signal is then filtered by the first 711*a* and second 711*b* colour filters such that light of only a first wavelength or wavelength range is permitted to pass from the fourth proportion of the light signal.

If there is no obstruction to the fourth proportion of the light signal transmitted across the passageway formed in the transfer tube 230 at the location of the first plurality of light directing elements 710, then the fourth proportion of the light signal will reach the multicolor sensor 750. On reaching the multicolor sensor 750, the multicolor sensor 750 not only detects generally the presence of the fourth proportion of the light signal but may, in some arrangements, detect specifically the presence of light in the first wavelength or wavelength range.

Conversely, if there is an obstruction to the fourth proportion of the light signal transmitted across the passageway formed in the transfer tube 230 at the location of the first plurality of light directing elements 710, then—as the skilled person will understand based upon the description of the sensing apparatus 200—the fourth proportion of the light signal will not be detected by the multicolor sensor 750. That is, no light in the first wavelength or wavelength range will be detected by the multicolor sensor 750. As result, it may be concluded that there is an obstruction at the location of the first plurality of light directing elements 710.

Accordingly, if—for example—the first 711*a* and second 711*b* filters filter red light, the second 721*a* and third 721*b* filters filter blue light, and the third 731*a* and fourth 731*b* filters filter yellow light, then the following will occur:

If there is an obstruction at the first further light directing elements 730, no red light will be detected by the multicolor sensor 750.

If there is an obstruction at the second further light directing elements 720, no blue light will be detected by the multicolor sensor 750.

If there is an obstruction at the first further light directing elements 710, no yellow light will be detected by the multicolor sensor 750.

If there are no obstruction at the 1st, 2nd or third light direction elements, all red and blue and yellow wave lengths will be detected.

Advantages

In addition to the advantages discussed in reference to the sensing apparatus 200, which also apply for the multipoint sensing apparatus 700, the multipoint sensing apparatus 700 also affords at least the following key advantage. Because it is possible to detect the position of a check cable or article 170 at three distinct points (that is, at each of the first, second and third further light directing elements 710, 720, 730) along the length of the apparatus 700, it is possible to verify that the check cable or article is 'arriving' at the next set of further light directing elements after the expected 'time'. In other words, after the check cable or article has been driven along the transfer tube 230 a certain distance. That certain distance could correspond, for example, with a certain angle of rotation of the drive mechanism 120, for example. This ability to verify the position of the check cable or article 170 is useful in improving the accuracy of the positioning of the check cable or radioactive source.

It also provides the possibility to supervise the tip of the wire. When the capsule is broken off the wire, you will see a large difference between encoder values, outwards and inwards.

Having two filters per set of light directing elements has the advantage that the accuracy of the detection by the multicolor sensor 750 is improved since the likelihood of interference from ambient light is reduced.

Alternatives

Although three sets of further light directing elements have been described here and are shown in FIG. 7, there may be any other number of further light directing elements equal or in excess of two. For example, there may be two sets of further light directing elements: one set akin to the second 720 or third 730 further light directing elements and distributed at some point along the length of the transfer tube 230, and one set akin to the first 710 further light directing elements and arranged at the second end of the transfer tube 230 (i.e. the end of the transfer tube 230 configured for coupling with the applicator 170).

In other examples, the elements in the second 720 and third 730 pluralities of light directing elements are approximately semi-circular in shape with a length in the direction of the axis of the transfer tube 230. The reason for the plurality of "prisms" or the semispheres, is that they are orientation independent to the light fibers, simplifying assembly.

FIG. 8

Figure 8:
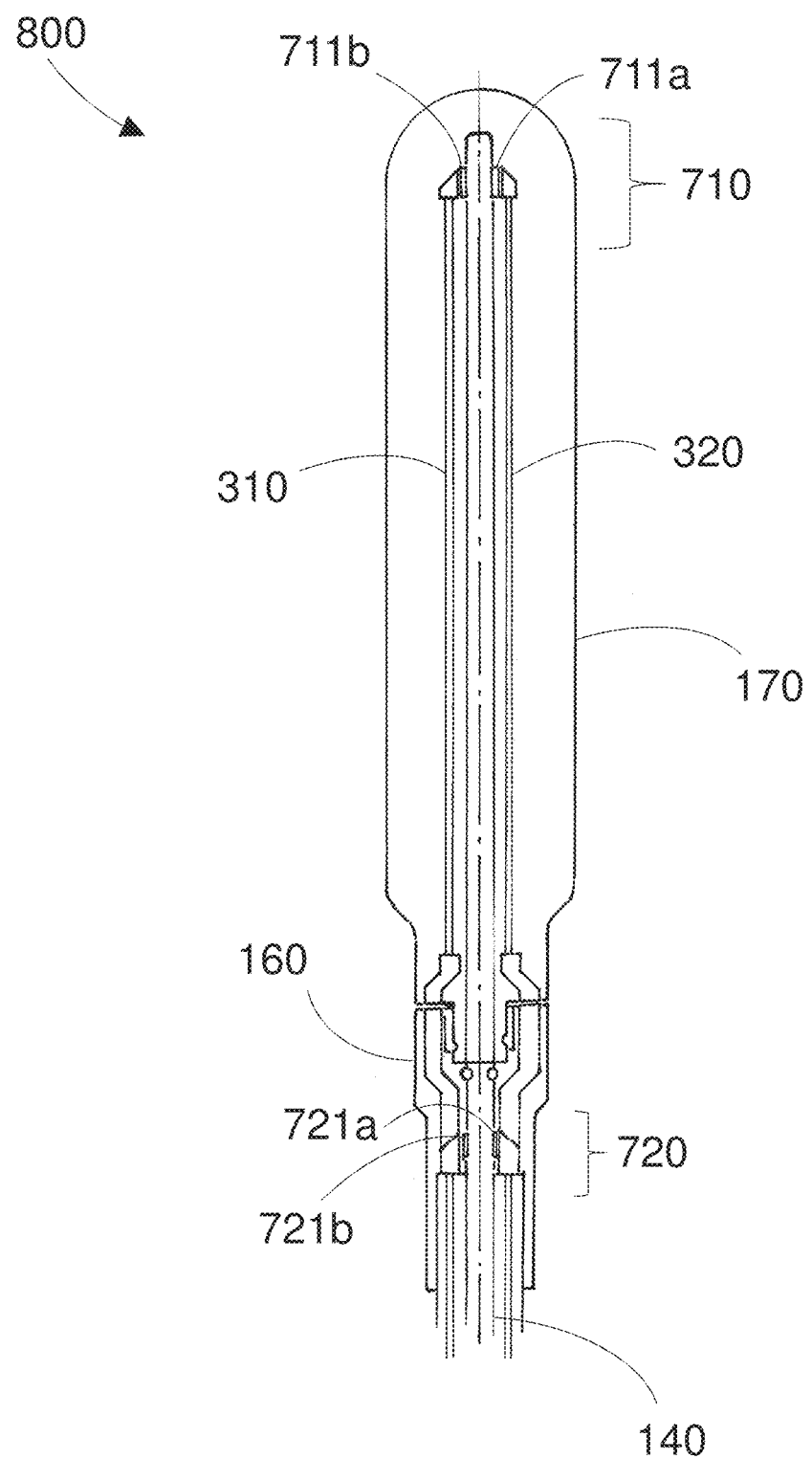
FIG. 8 is a sectional view of part of the sensing apparatus of FIG. 7 in an applicator.

FIG. 8 shows a sectional view of an alternative configuration of the sensing apparatus 700 in which the sensing apparatus 700 is distributed throughout: the transfer tube 230 (not indicated), the applicator transfer tube coupling 160, and the applicator 170.

In more detail, FIG. 8 shows the second further light directing elements 720 arranged as part of the applicator transfer tube coupling 160 and the first further light directing elements 710 arranged as part of the applicator 170. In this arrangement, the first 310 and second 320 optical fibre paths extend beyond the second end of the transfer tube 230 (i.e. beyond the end of the transfer tube 230 arranged for coupling with the applicator 170). As a result, signals in the first 310 and second 320 optical fibres can transmit the full length of the transfer tube 230 and applicator 170.

The first further light directing elements 710 (and associated first 711*a* and second 711*b* filters) are arranged substantially at the end of the applicator 170 which is furthest from that end arranged to couple with the transfer tube 230 (via the applicator transfer tube coupling 160). The second further light directing elements 720 (and associated third 721*a* and fourth 721*b* filters) meanwhile are arranged at the most proximate end of the transfer tube 230 arranged for coupling with the applicator 170—that is, at the second end of the transfer tube 230. In use however, the second further light directing elements 720 are housed within the applicator transfer tube coupling 160 region. Although not shown, the third further light directing elements (and associated fifth 721*a* and sixth 721*b* filters) are disposed at some other point along the length of the transfer tube 230.

In this example, as can be seen from FIG. 8, the applicator transfer tube coupling 160 includes mechanical fixings suitable for indexing each of the first 310 and second 320 optical fibres provided in the applicator transfer tube coupling 160 with the first 310 and second 320 optical fibres in the transfer tube 230, respectively. Similarly, these same mechanical fixings are suitable for indexing each of the first 310 and second 320 optical fibres provided in the applicator transfer tube coupling 160 with the first 310 and second 320 optical fibres in the applicator 170, respectively.

Advantages

An advantage of the arrangement described in relation to FIG. 8 is that, because of the distribution of the further light directing elements 710, 720, 730 between the transfer tube 230, applicator transfer tube coupling 160 and applicator 170, it can be detected if the article 150 has accidentally broken off the cable 140 inside the applicator 170. This is because, if the article 150 breaks off the cable 140 inside the applicator 170, then the obstruction between the second further light directing elements 720 will be removed 'sooner' than expected as the total length of the obstruction is now shorter by the length of the article 150 that has broken off. Thus, a light signal will be able to pass between the second 320 and first 310 optical fibres at the location of the second further light directing elements 720 at a time sooner than expected which corresponds to the change in total length of the obstruction. If this happens, it may be concluded that the article 150 has broken off somewhere between the first 710 and second 720 further light directing elements, and thus somewhere in the applicator 170. Evidently such knowledge is crucial to the accurate positioning and control of the article 150 at all times.

Further still, this distributed arrangement described in relation to FIG. 8 affords all of the advantages of the sensing apparatus 200 and the multiposition sensing apparatus 700. In particular, the second further light directing elements 720 can be used to set the zero-reference position from which the progression of the article 150 into the applicator 170 is measured. Accordingly, variations in the physical set up of the transfer tube 230 are still prevented from affecting the accuracy of the positioning of the article 150.

As will occur to the skilled person, the steps of the methods 1300 and 1400 described in relation to FIGS. 13 and 14 respectively apply equally well to the multipoint sensing apparatus 700.

FIG. 9

Figure 9:
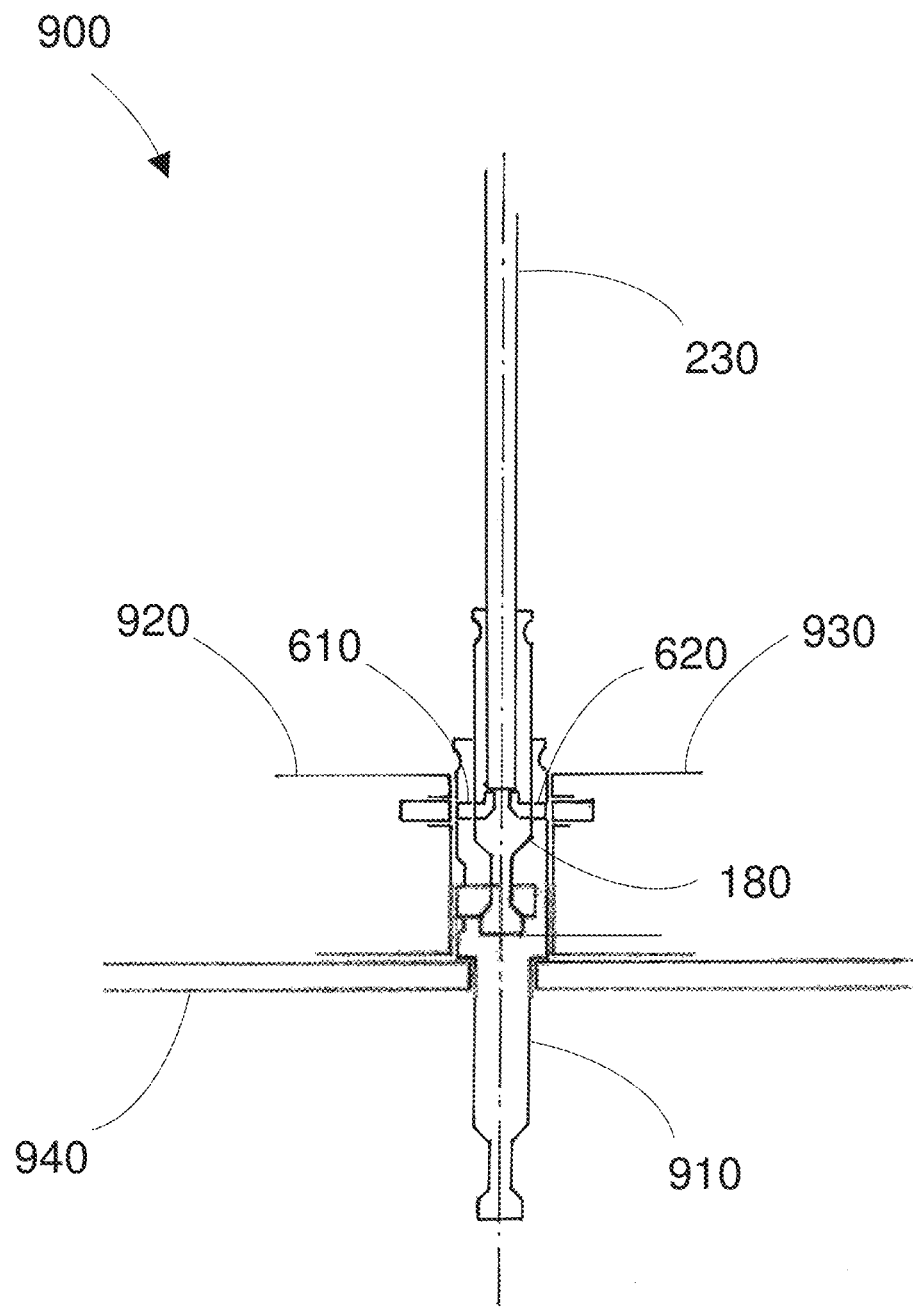
FIG. 9 is a sectional view of an afterloader transfer coupling adapter apparatus.

FIG. 9 shows a sectional view of an afterloader transfer coupling adaptor apparatus 900 that may be used with any of the previously described sensing apparatuses. The main benefit of the transfer coupling adaptor apparatus 900—and specifically adaptor 910—is that the transfer tube 230 of any of the described implementations may be retrofitted with an existing afterloader 110 which does not have an integrated source or sensor. This is by use of the adaptor 910 which acts as an extender plug to the afterloader transfer tube coupling 180. The afterloader transfer coupling adaptor apparatus 900 will now be described in more detail.

The afterloader transfer coupling adaptor apparatus 900 includes a transfer tube 230 according to any of the previously described implementations, further light transfer means 610, 620 as previously described, an external source 930, an external sensor 920, an afterloader transfer tube coupling 180 as previously described, a selector plate 930 and an adaptor 910.

The further light transfer means 610, 620 interface with the transfer tube 230 as previously described. The further light transfer means 610, 620 and transfer tube 230 are each partially housed in the afterloader transfer tube coupling 180. The afterloader transfer tube coupling 180 has a first end which is connected with the transfer tube 230 and a second end which is arranged to connect with the afterloader 110.

The external source 930 and the external sensor 920 are provided external to the afterloader 110. Both the external source 930 and the external sensor 920 are arranged either side of the afterloader transfer tube coupling 180 (and thus transfer tube 230) and are arranged proximate to the selector plate 930 of the afterloader 110.

The adaptor 910 has an overall shape similar to that of a headphone jack. The adaptor 910 has an inlet at a first end and a projection at a second end. The inlet at the first end is suitably shaped and sized to receive and secure to the second end of the afterloader transfer tube coupling 180. The projection at the second end is suitably sized and shaped for inserting into the afterloader 110. The adaptor 910 has an internal passageway extending along its length which has a diameter approximately equivalent to the diameter of the transfer tube 230. This is so that, in use, a cable or article 150 may pass through the adaptor 910 and into the transfer tube 230 (via the afterloader transfer tube coupling 180).

As noted above, in use, the projection of the adaptor 910 is inserted into a socket in the afterloader 110. The inlet of the adaptor 910 meanwhile receives the second end of the afterloader transfer tube coupling 180.

The further light transfer means 610, 620 each interface with the external sensor 920 and external source 930, respectively.

In use, the sensor apparatus 200, 700 employed with the afterloader transfer tube coupling 180 functions in substantially the same way as previously described.

In some examples, the driving of the cable or article 150 is measured from the plane of the sensor and sensing device. Therefore, when the coupling 180 is inserted directly into the afterloader 110 (that is, without use of the adaptor 910), the driving is measured from a plane which extends within the applicator 110. Whereas when the coupling 180 is inserted into the afterloader 110 via the adaptor 910, the driving is measured from a plane which extends external to and which does not intercept the applicator 110.

Leading on from this, when the adaptor 910 is used, the distance between the base of the connector 180 and the base of the adaptor 910 is a known amount. This known amount is added to the length of the distance that the delivery tube must travel.

Advantages

The adaptor 910 has the advantage that the previously described implementations—and particularly the transfer tubes 230 of the previously described implementations—may be used with an afterloader 110 not having a sensor or light source. This is because the adaptor 910 acts as an extender and relocates the further light directing elements 610, 620 from accepting and emitting light into a space inside the afterloader 100 to accepting and emitting light into a space external to the afterloader 100. As a result, an external light source and sensor may be placed in a space external to the afterloader. Accordingly, the adaptor 910 allows retrofitting of a transfer tube 230 according to the described implementations.

FIG. 10

Figure 10:
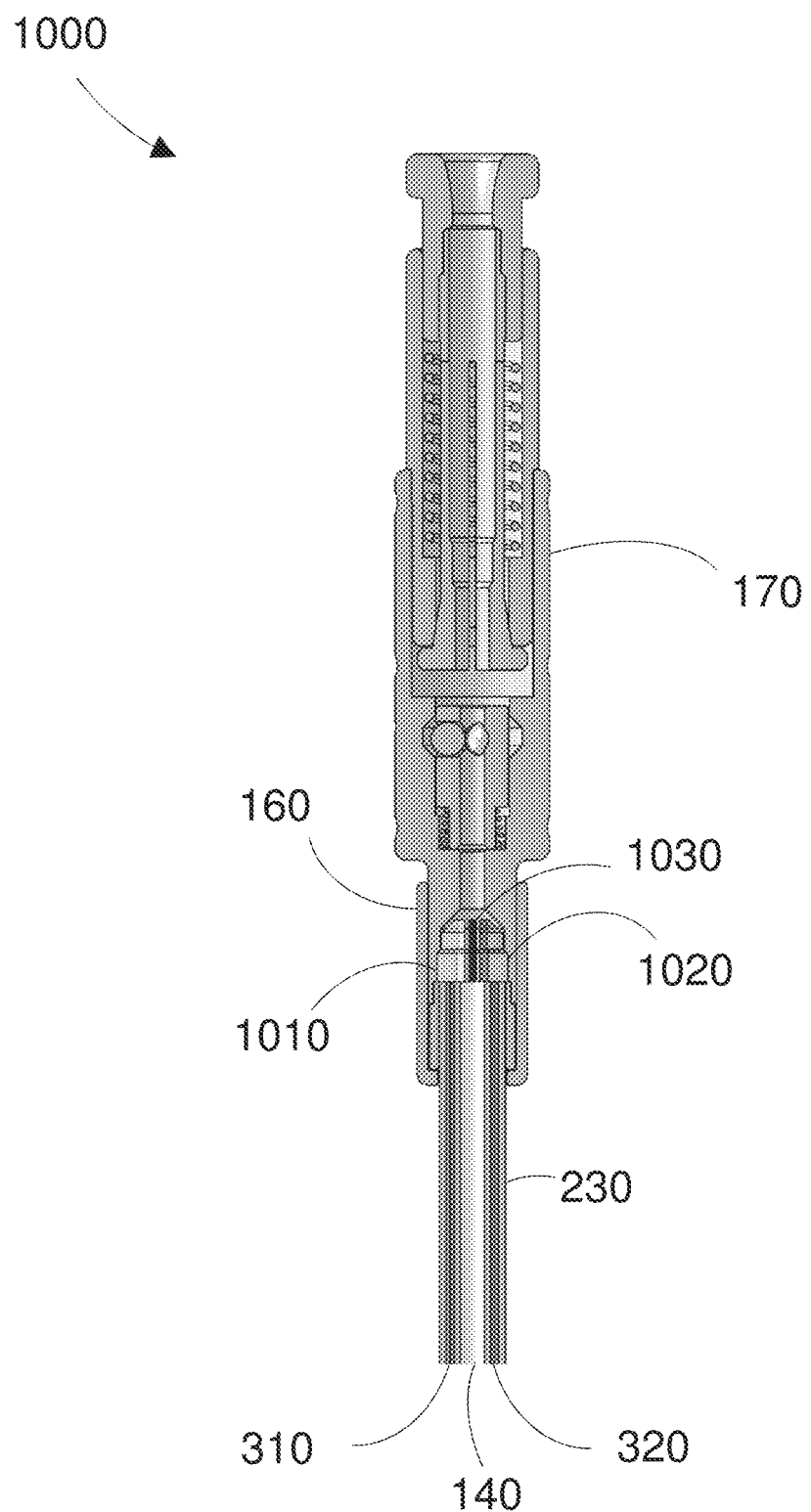
FIG. 10 is a sectional view of part of a sensing apparatus that is a third implementation.

FIG. 10 shows a sectional view of part of a sensing apparatus 1000 that is a third implementation. As will become apparent from the following description, features of the sensing apparatus 1000 may be employed in the sensing apparatuses according to the first and second implementations.

In more detail, FIG. 10 shows a transfer tube 230 which is substantially the same as the transfer tube 230 of the sensing apparatus 200. The second end of the transfer tube 230 is inserted into an applicator transfer tube coupling 160 as previously described. The signal transfer means 300 is arranged at this second end of the transfer tube 230 inserted into the applicator transfer tube coupling 160 and so the signal transfer means 300 is housed in the coupling region. In this arrangement however, there are two main modifications:

a. The plurality of light directing elements 410a-f described in relation to the sensing apparatus 200 are replaced with two light directing elements: a first light directing element 1010 and a second light directing element 1020. The first light directing element 1010 interfaces with the first optical fibre 310. The second light directing element 1020 interfaces with the second optical fibre 320. The first and second light directing elements 1010, 1020 will be described in more detail in reference to FIG. 12.

b. The first and second light directing elements are separated by two light isolators: a first isolator 1030 and a second isolator (now shown). The light isolators will be described in more detail in reference to FIG. 12.

Figure 11:
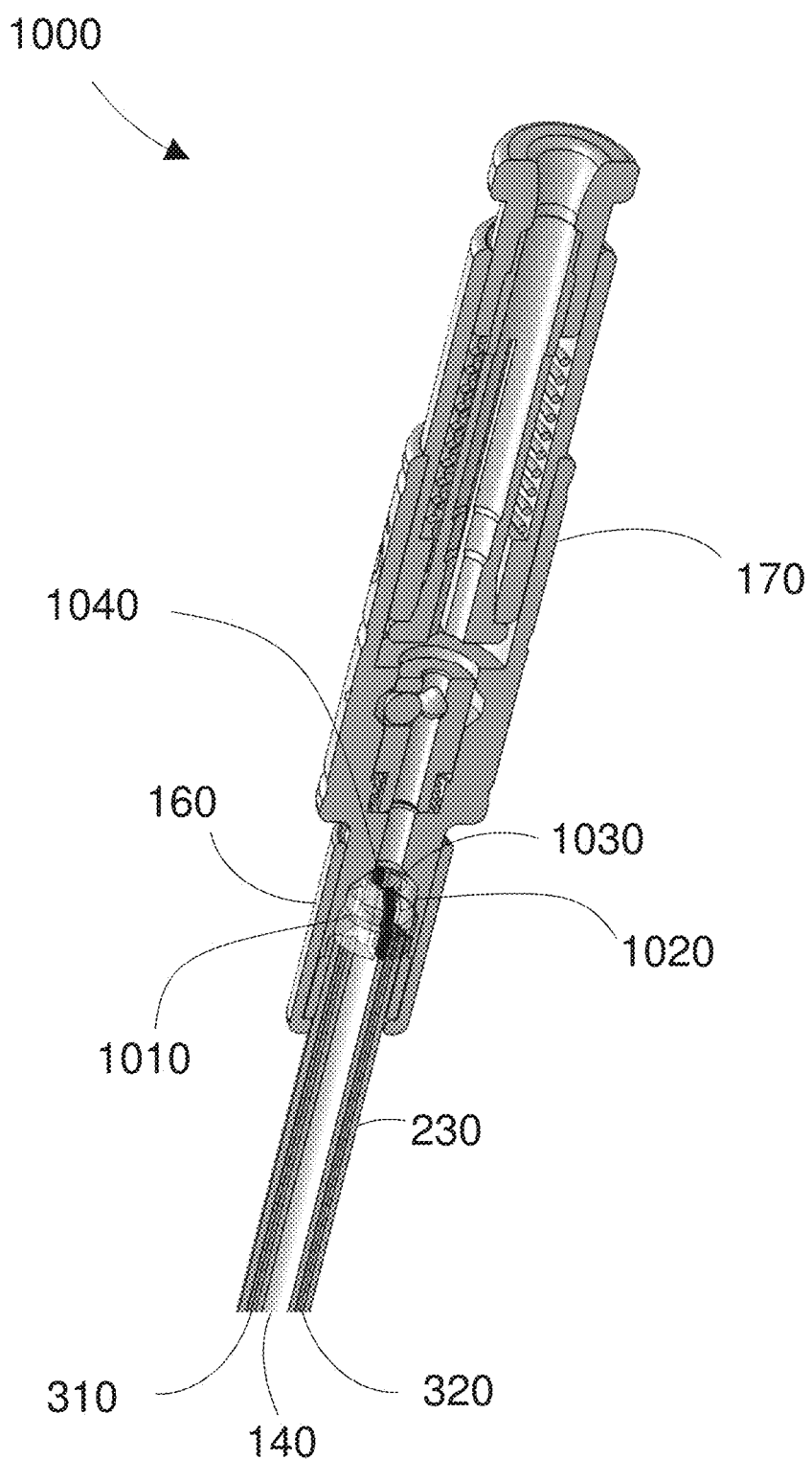
FIG. 11 is an axonometric sectional view of the part of the sensing apparatus of FIG. 10.

FIG. 11 shows an axonometric sectional view of the part of the sensing apparatus 1000. From FIG. 11 both the first 1030 and second 1040 light isolators can be seen.

Figure 12:
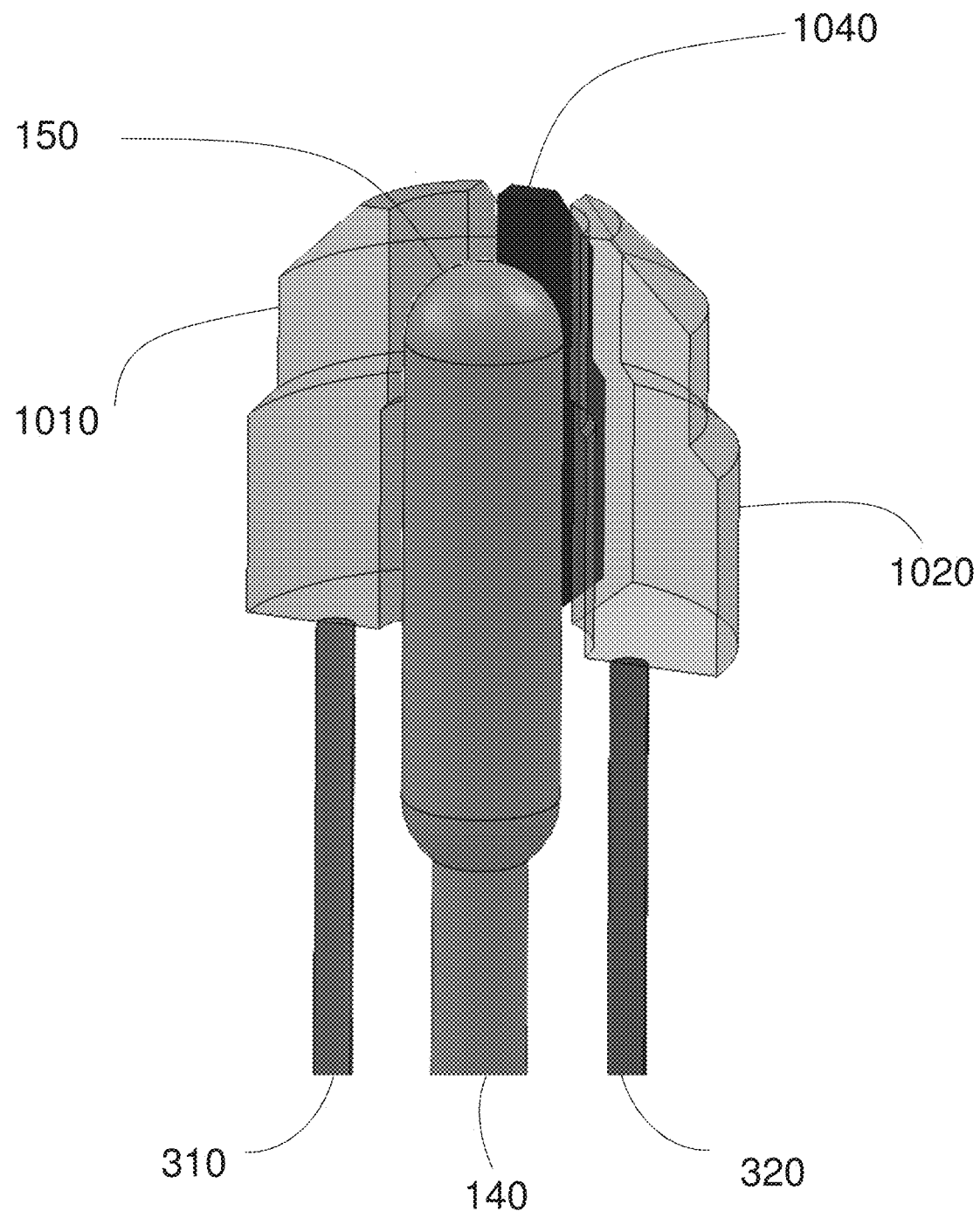
FIG. 12 is an axonometric sectional view of light transfer means of the part of the sensing apparatus of FIG. 10.

FIG. 12 shows an axonometric sectional view of the first 1010 and second 1020 light directing elements of the part of sensing apparatus of FIG. 10 in more detail. The first 1030 and second 1040 light isolators are disposed between the first 1010 and second 1020 light directing elements.

The shape of the first 1010 and second 1020 light directing elements is generally similar to that of the plurality of light directing elements 410a-f, however each of the first 1010 and second 1020 light directing elements extends around approximately 160 degrees of the wall of the transfer tube 230.

The shape of the first 1030 and second 1040 light isolators is also generally similar to that of the plurality of light directing elements 410a-f, however each of the first 1010 and second 1020 light isolators extends around approximately degrees of the wall of the transfer tube 230.

As mentioned above, the first 1030 and second 1040 light isolators are disposed between the first 1010 and second 1020 light directing elements such that the order of the components disposed around the transfer tube 230 wall in a clockwise direction is: the first light isolator 1030; the first light directing element 1030; the second light isolator 1040; and the second light directing element 1020. Accordingly, the first 1030 and second 1040 light isolators are opposite each other and the first 1010 and second 1020 light directing elements are opposite each other. The first 1030 and second 1040 light isolators are each formed of an opaque material which does not allow light to pass through.

Advantages

The advantage of employing the first 1030 and second 1040 light isolators is that no light may pass between the first 1010 and second 1020 light directing elements around the circumference of the transfer tube 230. Instead, light may only transfer between the first 1010 and second 1020 light directing elements across the diameter of the transfer tube 230—and thus across the passageway formed inside the transfer tube 230. Usefully, this improves reliability as the frequency of false readings at the sensor 630, 750 are reduced. In the absence of the first 1030 and second 1040 light isolators, a false reading could arise if there is an obstruction in the passageway of the transfer tube 230 at the location of the first 1010 and second 1020 light directing elements, but a light signal still transfers between the first 1010 and second 1020 light directing elements around the circumference of the transfer tube 230. In this scenario, the sensor 630, 750 might detect a light signal and so determine that there is no obstruction at the location of the first 1010 and second 1020 light directing elements, when in fact there is.

A benefit of having only two light directing elements is that the manufacture and assembly process is simplified. Manufacture is simplified as fewer components need to be made to achieve the desired functionality. Assembly is simplified as only two light directing elements need to be arranged around the transfer tube 230 interfacing with the optical fibres. This results in fewer assembly operations and so reduces the opportunity for error and failure.

In all of the above described implementations and examples, the 'light' and the 'signal' may be non-visible signals. For example, the signals may be infrared signals, for example. The advantage of using non-visible signals, such as infrared, is that interference from ambient light is reduced.

As will be clear to the skilled person, a variety of different types of light directing element have been described. Combinations of these types may be employed in sensing apparatus as will occur to the skilled person.

As the skilled person will appreciate, there may be some efficiency loss in the transfer of the signals, such as light signals, such that not all light transmitted into the second optical fibre 320 is subsequently received by the first optical fibre 310, for example. This does not affect the functioning of the described apparatus (unless the efficiency loss is so great that no light or insufficient light is received back at the sensor despite there not being an obstruction in the transfer tube 230).

While reference is made herein to 'light' and 'colours' of light, it will be appreciated that electromagnetic radiation of any frequency may be used, for example UV and infrared.

In the above described implementations, all "means" may—as the skilled person will appreciate—be specific apparatuses. An example of a specific apparatus has been given in each case.

The following examples may further characterize the invention:

Example 1. A transfer tube through which an article may travel for use in a brachytherapy procedure, the transfer tube comprising:

a first end connectable to an afterloader; and a second end connectable to an applicator, the second end being downstream of the first end; and signal transfer means operable with sensing means to detect the presence of the article at a point downstream of the first end of the transfer tube.

Example 2. The transfer tube of example 1, wherein the signal transfer means is operable with the sensing means to detect the presence of the article as it exits the transfer tube via the second end.

Example 3. The transfer tube of example 1 or example 2, wherein the point is located in the applicator.

Example 4. The transfer tube of any preceding example, wherein the point is located along the transfer tube.

Example 5. The transfer tube of any preceding example, wherein the point is located nearer to the second end of the transfer tube than the first end of the transfer tube.

Example 6. The transfer tube of any preceding example, wherein the point is located substantially at the second end of the transfer tube.

Example 7. The transfer tube of example 6, wherein the transfer tube defines at least part of a path along which the article may travel, and the signal transfer means is configured to transfer a signal across the path which may be interrupted by the presence of the article at the point.

Example 8. The transfer tube of any preceding example, wherein the signal transfer means comprises at least two optical fibres, optionally wherein the at least two optical fibres are embedded in the wall of the transfer tube.

Example 9. The transfer tube of example 8, wherein the signal transfer means further comprises light transfer means arranged at the point, and wherein the at least two optical fibres are coupled with the light transfer means, and wherein at least one of the at least two optical fibres is coupled with the sensing means.

Example 10. The transfer tube of example 9, wherein the light transfer means is operable to transfer light between the at least two optical fibres.

Example 11. The transfer tube of example 10, wherein:
a first optical fibre of the at least two optical fibres is configured to receive light from a light source and transfer the light to the light transfer means;
the light transfer means is configured to transfer the light from the first to a second optical fibre of the at least two optical fibres; and
the second optical fibre is configured to transfer the light from the light transfer means to the sensing means.

Example 12. The transfer tube of any preceding example wherein, in use, the article travels from the afterloader, into the transfer tube at the first end of the transfer tube, along the transfer tube to the second end of the transfer tube, and into the applicator, such that the second end of the transfer tube and the applicator are downstream of the first end of the transfer tube.

Example 13. A sensing apparatus for sensing the presence of an article at a point along the sensing apparatus during a brachytherapy procedure, the sensing apparatus comprising:
a transfer tube comprising a first end and a second end, the second end being downstream of the first end; and
sensing means operable to detect the presence of the article at a point downstream of the first end of the transfer tube.

Example 14. The sensing apparatus of example 13, wherein the transfer tube is the transfer tube of any of examples 1 to 12.

Example 15. The sensing apparatus of example 13 or example 14, wherein, in use, the article enters the transfer tube through the first end of the transfer tube and exits the transfer tube through the second end of the transfer tube.

Example 16. The sensing apparatus of any of examples 13 to 15, wherein the point is located along the transfer tube.

Example 17. The sensing apparatus of any of examples 13 to 16, wherein the point is located substantially at the second end of the transfer tube.

Example 18. The sensing apparatus of any of examples 13 to 17, the apparatus further comprising:
an applicator positioned downstream of the first end of the transfer tube.

Example 19. The sensing apparatus of example 18, the applicator comprising a first end and a second end, the second end of the transfer tube being connectable to the first end of the applicator, and wherein the point is located between the first and second ends of the applicator.

Example 20. The sensing apparatus of any of examples 13 to 19, wherein the sensor is operable to detect the presence of the article at a plurality of points downstream of the first end of the transfer tube.

Example 21. The sensing apparatus of any of examples 13 to 20, further comprising a light source, and wherein the transfer tube further comprises:
a first optical fibre configured to receive light from the light source and transfer the light to light transfer means located at the point, the light transfer means being configured to transfer the light from the first optical fibre to a second optical fibre; and
wherein the second optical fibre is configured to transfer the light from the light transfer means to the sensing means.

Example 22. A method of sensing the presence of an article at a point along brachytherapy apparatus during a brachytherapy procedure, the brachytherapy apparatus defining a path along which the article may travel and comprising:
a transfer tube comprising a first end connectable to an afterloader and a second end connectable to an applicator, the second end being downstream of the first end; and
signal transfer means operable with sensing means to detect the presence of the article at the point downstream of the first end of the transfer tube, the method comprising:
sending, from a source, a signal to the sensing means via the signal transfer means; the signal transfer means being configured to transfer the signal across the path;
determining if the signal is received at the sensing means; and
if the signal is not received at the sensing means, determining that the article is at the point downstream of the first end of the transfer tube.

Example 23. The method of example 22, further comprising:
if the signal is not received at the sensing means, sending, from the sensing means to control means, a signal indicating that the article is at the point downstream of the first end of the transfer tube, wherein the control means is operable to control a drive mechanism and the drive mechanism is operable to drive the article through the brachytherapy apparatus.

Example 24. The method of example 23, further comprising:
upon receipt at the control means of the signal indicating that the article is at the point downstream of the first end of the transfer tube, sending, from the control means to the drive mechanism, an instruction to drive the article a predetermined distance from the point.

Example 25. The method of example 24, further comprising:
upon receipt at the drive mechanism of the instruction to drive the article the predetermined distance from the point, driving, by the drive mechanism, the article the predetermined distance from the point.

Example 26. A computer-readable medium comprising computer executable instructions for carrying out the method of any of examples 22 to 25.

The above implementations have been described by way of example only, and the described implementations and arrangements are to be considered in all respects only as illustrative and not restrictive. It will be appreciated that variations of the described implementations and arrangements may be made without departing from the scope of the invention and that such variations are envisaged and intended to be within the scope of the present disclosure.

The approaches described herein may be embodied on a computer-readable medium, which may be a non-transitory computer-readable medium. The computer-readable medium carrying computer-readable instructions arranged for execution upon a processor so as to make the processor carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge

The invention claimed is:

1. A sensing apparatus for sensing a presence of an article at a point along the sensing apparatus during a brachytherapy procedure, the sensing apparatus comprising:
   a transfer tube defining at least part of a path through the transfer tube along which an article may travel for use in a brachytherapy procedure, the transfer tube comprising:
      a first end connectable to an afterloader;
      a second end connectable to an applicator, the second end being downstream of the first end;
      signal transfer means operable with sensing means to detect the presence of the article at a point downstream of the first end of the transfer tube, wherein the signal transfer means is operable with the sensing means to detect the presence of the article as it exits the transfer tube via the second end, wherein the signal transfer means is configured to transfer a signal across the path which may be interrupted by the presence of the article at the point; and
      a zero reference point controller arranged to control progression of the article into the applicator relative to a zero reference point formed by the point downstream of the first end of the transfer tube, wherein the sensing means is configured to send the zero reference point controller a signal indicating that the article is at the point, and the zero reference point controller is configured to send an instruction to a drive mechanism to drive the article into the applicator by a predetermined distance from the point.

2. The sensing apparatus of claim 1, wherein the signal transfer means comprises at least two optical fibres, optionally wherein the at least two optical fibres are embedded in a wall of the transfer tube, wherein a first optical fibre of the at least two optical fibres is configured to receive light from a light source and transfer the light to a light transfer means, wherein the light transfer means is configured to transfer the light from the first optical fibre to a second optical fibre of the at least two optical fibres, and wherein the second optical fibre is configured to transfer the light from the light transfer means to the sensing means.

3. The sensing apparatus of claim 2, wherein the signal transfer means further comprises the light transfer means arranged at the point, and wherein the at least two optical fibres are coupled with the light transfer means, and wherein at least one of the at least two optical fibres is coupled with the sensing means, wherein the light transfer means is operable to transfer light between the at least two optical fibres, and wherein the light transfer means comprises a base element in optical contact with each of the first optical fibre and the second optical fibre.

4. The sensing apparatus of claim 3, wherein the light transfer means comprises:
   one or more light directing elements optically connected to the base element, that are semi-circular in shape with a length in a direction of an axis of the transfer tube.

5. The sensing apparatus of claim 4, wherein the one or more light directing elements are formed by a number of isosceles trapezoid shapes that taper to a point proximate to an inner diameter of the transfer tube which defines an outer diameter of an internal passageway for the article.

6. The sensing apparatus of claim 4 wherein the one or more light directing elements are cuboidal in shape.

7. The sensing apparatus of any of claim 5, wherein the one or more light directing elements are separated by light isolators.

8. The sensing apparatus of claim 1, wherein, in use, the article travels from the afterloader, into the transfer tube at the first end of the transfer tube, along the transfer tube to the second end of the transfer tube, and into the applicator, such that the second end of the transfer tube and the applicator are downstream of the first end of the transfer tube.

9. The sensing apparatus of claim 1 further comprising a drive mechanism.

10. A method of sensing the presence of an article at a point along brachytherapy apparatus during a brachytherapy procedure, the brachytherapy apparatus defining a path along which the article may travel and comprising:
    a transfer tube comprising a first end connectable to an afterloader and
    a second end connectable to an applicator, the second end being downstream of the first end; and
    signal transfer means operable with sensing means to detect the presence of the article at the point downstream of the first end of the transfer tube, wherein the signal transfer means is operable with the sensing means to detect the presence of the article as it exits the transfer tube via the second end the method comprising:
    sending, from a source, a signal to the sensing means via the signal transfer means; the signal transfer means being configured to transfer the signal across the path;
    determining if the signal is received at the sensing means; and if the signal is not received at the sensing means, determining that the article is at the point downstream of the first end of the transfer tube; and
    controlling, by a zero reference point controller, the progression of the article into the applicator relative to a zero reference point formed by the point downstream of the first end of the transfer tube, by sending, from the controller, an instruction to drive the article a predetermined distance from the point.

11. The method of claim 10, further comprising:
    if the signal is not received at the sensing means, sending, from the sensing means to control means, a signal indicating that the article is at the point downstream of the first end of the transfer tube, wherein the control means is operable to control a drive mechanism and the drive mechanism is operable to drive the article through the brachytherapy apparatus.

12. The method of claim 10, further comprising:

upon receipt at the control means of the signal indicating that the article is at the point downstream of the first end of the transfer tube, sending, from the control means to the drive mechanism, an instruction to drive the article a predetermined distance from the point.

13. The method of claim 10, further comprising:

upon receipt at the drive mechanism of the instruction to drive the article the predetermined distance from the point, driving, by the drive mechanism, the article the predetermined distance from the point.

14. The method of claim 10, further comprising:

when the article is retracted towards the drive mechanism, and before reaching the predetermined distance from the point, the signal indicating the point is reached already, it is concluded the article lost its integrity, alerting the need for corrective actions from the operator and/or from service personnel.

* * * * *